(12) United States Patent
Doten et al.

(10) Patent No.: US 6,539,316 B1
(45) Date of Patent: Mar. 25, 2003

(54) PHASE DETECTOR

(75) Inventors: Gregory P. Doten, Crystal, MN (US); Ronald E. Patton, Straubing (DE)

(73) Assignee: Data Sciences International, Inc., Arden Hills, MN (US)

( * ) Notice: Subject to any disclaimer, the term of this patent is extended or adjusted under 35 U.S.C. 154(b) by 0 days.

(21) Appl. No.: 09/478,486

(22) Filed: Jan. 6, 2000

(51) Int. Cl.[7] .................................................. G06F 7/02
(52) U.S. Cl. ............................ 702/48; 702/33; 702/38; 702/39; 702/45; 702/46; 702/47
(58) Field of Search ........................ 73/861.25–861.92; 327/3–4, 6, 9, 18, 22, 23, 91, 94, 174–175, 536; 702/33, 38–39, 45–48, 50, 54–56, 72, 100, 103

(56) References Cited

U.S. PATENT DOCUMENTS

| | | |
|---|---|---|
| 3,575,050 A | 4/1971 | Lynnworth et al. |
| 4,001,603 A | 1/1977 | Wilcox ...................... 3037/232 |
| 4,001,680 A | 1/1977 | Bylund et al. ................. 324/78 |
| 4,011,503 A | 3/1977 | Ferrara ......................... 324/83 |

(List continued on next page.)

FOREIGN PATENT DOCUMENTS

| | | |
|---|---|---|
| CA | 1153795 | 9/1983 |
| DE | 19617635 | 11/1997 |
| EP | 0012058 | 6/1980 |
| EP | 0252444 | 7/1987 |
| EP | 0402711 | 12/1990 |
| EP | 0588599 | 3/1994 |
| EP | 0711041 | 11/1994 |
| EP | 0803984 | 3/1997 |

OTHER PUBLICATIONS

"Transonic Extracorporeal Products", http://www.transonic.com/body extracorporeal.html, Transonic Systems Inc., Ithaca, NY, 7 p., (1996).

"Manual for SYSTEM 5 SVT2 MODULE, Triton Technology, Inc.,", 1–18, (Jun. 16, 1997).

Drost, C.J., "Vessel Diameter–Independent Volume Flow Measurements Using Ultrasound", *Proceedings of the San Diego Biomedical Symposiom (J. Martin et al., Eds.), vol. 17*, 299–302, (1978).

Hartley, C.J., "A Phase Detecting Ultrasonic Flowmeter", *25th ACEMB –Americana Hotel, Bal Harbour, Florida, Oct. 1–5, 1972*, Supported by NIH Grant HE–03251–08.,7 pages.

Nagata, M., "A PWM Signal Processing Core Circuit Based on a Switched Current Integration Technique", *IEEE Journal of Solid–State Circuits, vol. 33, No. 1*, pp. 53–60, (Jan. 1998).

Johansson, H., "A Simple Precharged CMOS Phase Frequency Detector", *IEEE Journal of Solid–State Circuits, 33 (2)*, pp. 295–299, (Feb. 1998).

Maeda, T., et al., "An Ultra–Low–Power–Consumption High–Speed GaAs Quasi–Differential Switch Flip–Flop (QD–FF)", *IEEE Journal of Solid–State Circuits, 31 (9)*, pp. 1361–1363, (Sep. 1996).

Rothermel, A., et al., "Analog Phase Measuring Circuit for Digital CMOS IC'S", *IEEE Journal of Solid–State Circuits, 28(7)*, pp. 853–856, (Jul. 1993).

(List continued on next page.)

*Primary Examiner*—Marc S. Hoff
*Assistant Examiner*—Felix Suarez
(74) *Attorney, Agent, or Firm*—Schwegman, Lundberg, Woessner & Kluth, P.A.

(57) ABSTRACT

A method for detecting a phase difference between first and second input signals is provided. The method includes modulating a duty cycle of first and second intermediate signals from a first duty cycle based on the phase difference between the first and second input signals. The method further includes creating a differential output signal based on the modulated duty cycles of the first and second intermediate signals that is related to the phase difference between the first and second input signals.

38 Claims, 12 Drawing Sheets

U.S. PATENT DOCUMENTS

| | | | |
|---|---|---|---|
| 4,015,470 A | 4/1977 | Morrison | 73/194 A |
| 4,022,058 A | 5/1977 | Brown | 73/194 |
| 4,055,814 A * | 10/1977 | Abraham et al. | 327/147 |
| 4,068,184 A | 1/1978 | Ahmed | 330/257 |
| 4,109,523 A | 8/1978 | Teyssandier | 73/194 A |
| 4,185,498 A * | 1/1980 | Watson et al. | 73/597 |
| 4,194,166 A | 3/1980 | Sakai et al. | 330/257 |
| 4,227,407 A | 10/1980 | Drost | 73/194 |
| 4,265,126 A | 5/1981 | Papadofrangakis et al. | 73/861 |
| 4,308,754 A | 1/1982 | Pedersen et al. | 73/861.28 |
| 4,312,238 A | 1/1982 | Rey | 73/861.28 |
| 4,316,150 A | 2/1982 | Crosby | 331/1 A |
| 4,365,204 A | 12/1982 | Haque | 328/127 |
| 4,383,202 A | 5/1983 | Beck et al. | 315/200 A |
| 4,384,491 A * | 5/1983 | Brown et al. | 73/861.28 |
| 4,520,319 A | 5/1985 | Baker | 328/133 |
| 4,524,333 A | 6/1985 | Iwata et al. | 331/17 |
| 4,557,148 A | 12/1985 | Akiyama | 73/861.28 |
| 4,585,989 A | 4/1986 | Matney | 324/83 |
| 4,629,914 A | 12/1986 | Okanobu | 307/510 |
| 4,633,719 A | 1/1987 | Vander | 73/861.28 |
| 4,808,856 A | 2/1989 | Tanigawa | 307/511 |
| 4,870,303 A | 9/1989 | McGinn | 328/155 |
| 4,922,750 A | 5/1990 | Magori | |
| 4,947,852 A | 8/1990 | Nassi et al. | 128/662.06 |
| 5,035,147 A | 7/1991 | Woodward | 73/861.28 |
| 5,078,148 A | 1/1992 | Nassi et al. | 128/661.09 |
| 5,103,123 A | 4/1992 | McGinn | 307/514 |
| 5,117,698 A | 6/1992 | Baumoel | 73/861.28 |
| 5,121,639 A * | 6/1992 | McShane | 73/195 |
| 5,121,749 A | 6/1992 | Nassi et al. | 128/692 |
| 5,142,555 A | 8/1992 | Whiteside | 375/81 |
| 5,200,980 A | 4/1993 | Briddell | 375/83 |
| 5,339,816 A | 8/1994 | Akamatsu et al. | 128/661.09 |
| 5,440,936 A | 8/1995 | Spani et al. | 73/861.28 |
| 5,461,921 A | 10/1995 | Papadakis et al. | |
| 5,515,721 A | 5/1996 | Kim et al. | 73/170.13 |
| 5,553,505 A | 9/1996 | Bignell et al. | 73/861.28 |
| 5,577,079 A | 11/1996 | Zenno et al. | 375/373 |
| 5,585,756 A | 12/1996 | Wang | 327/341 |
| 5,659,268 A | 8/1997 | Kesner | 331/1 A |
| 5,663,666 A | 9/1997 | Chu et al. | 327/7 |
| 5,669,685 A | 9/1997 | Kotani et al. | 353/28 |
| 5,694,062 A | 12/1997 | Welch et al. | 327/3 |
| 5,695,092 A | 12/1997 | Schrandt | |
| 5,747,689 A | 5/1998 | Hampo et al. | |
| 5,757,868 A | 5/1998 | Kelton et al. | 375/360 |
| 5,767,736 A | 6/1998 | Lakshmikumar et al. | 127/536 |
| 5,774,084 A | 6/1998 | Brombaugh et al. | 341/152 |
| 5,785,657 A | 7/1998 | Breyer et al. | 600/454 |
| 5,865,749 A * | 2/1999 | Doten et al. | 600/443 |
| 5,953,386 A | 9/1999 | Anderson | 375/376 |
| 5,970,106 A | 10/1999 | Izumikawa | 375/376 |
| 6,183,423 B1 * | 2/2001 | Gaumond | 600/529 |
| 6,346,081 B1 | 2/2002 | Vilkomerson | 600/454 |

OTHER PUBLICATIONS

Somasekhar, D., et al., "Differential Current Switch Logic: A Low Power DCVS Logic Family", *IEEE Journal of Solid–State Circuits, 31(7)*, pp.; 981–991, (Jul. 1996).

Soyuer, M., et al., "High–Frequency Phase–Locked Loops in Monolithic Bipolar Technology", *IEEE Journal of Solid–State Circuits, 24(3)*, pp. 787–795, (Jun. 1989).

* cited by examiner

PHASE DETECTOR

CROSS REFERENCE TO RELATED CASES

This application is related to the following commonly assigned, co-pending applications:

Application Ser. No. 09/478,762, entitled "ESTIMATION OF ERROR ANGLE IN ULTRASOUND FLOW MEASUREMENT" and filed on Jan. 6, 2000 (the '045 Application); and Application Ser. No. 09/479,268, entitled "MULTI-PLEXED PHASE DETECTOR" and filed on Jan. 6, 2000 (the '046 Application);

The '045 and '046 Applications are incorporated herein by reference.

TECHNICAL FIELD OF THE INVENTION

The present invention relates generally to the field of electronic circuits and, in particular, to a phase detector.

BACKGROUND

Phase detectors detect or measure the relative phase of two signals with respect to each other, and are used in a wide variety of electronic systems. For example, a phase detector is a fundamental building block for a phase lock loop (PLL) found in many electronic systems. A PLL is particularly useful in demodulating radio frequency (RF) signals in, for example, an FM radio receiver.

A PLL is a circuit that causes a particular system to track with another system. More particularly, a PLL is a circuit that synchronizes an output signal (generated by an oscillator) with a reference or input signal in frequency as well as in phase. A typical PLL includes three main building blocks: a phase detector, a loop filter and a voltage (or current) controlled oscillator. The phase detector receives the reference or input signal as well as the output of the voltage controlled oscillator. The phase detector measures the phase difference between the input signal and the output signal of the voltage controlled oscillator. The phase difference acts as an error signal that is fed to the voltage controlled oscillator via the loop filter. When, the phase detector detects zero, or very small, phase error between the input or reference signal and the output of the oscillator, the PLL is said to be locked.

Common types of phase detectors include analog multiplier circuits such as the Gilbert cell and ring diode mixer topologies. These phase detectors typically accept sinusoidal input signals. Other phase detectors accept digital input signals. For example, exclusive OR gate and RS Flip-Flop phase detectors fall into this category. The detectors produce a duty cycle modulated output whose average value is proportional to the phase difference. A last type of detector is the Sequential Phase/Frequency Detector. This type of detector produces two outputs, the first (second) labeled as up (down). These two outputs are individually duty cycle modulated depending on which input is leading and the magnitude of the phase difference.

Phase detectors are used in a number of conventional applications requiring continuous measurement of phase error control, e.g., a Voltage Controlled Oscillator (VCO). Other applications include using a phase detector to measure the change in phase in a Phase Shifted Keying (PSK) communications system where the digital data is encoded in the phase of the transmitted signal. These examples show applications where the measurement of phase is important, but not necessarily the precise measurement of phase. An application, which requires a precise measurement of phase, is a Transit Time flow meter.

A Transit Time flow meter estimates volumetric flow by measuring the phase difference between bursts of ultrasound traveling upstream, and downstream paths across a tube with moving fluid. The phase difference is dependent on the volumetric flow when the entire tube or vessel is illuminated with the sound waves. Papers published by Craig Hartley, Ph.D., or Cor Drost, Ph.D., explain that the moving fluid causes the time required by the sound waves to travel across the vessel to be different for an upstream and downstream path when the fluid is moving. In other words, when the same signal is transmitted on the upstream and downstream paths, a phase difference is introduced between the two received signals by the motion of the fluid.

Transonics Systems Inc., a commercial supplier of Transit-Time flow measurement equipment, measures the phase shift with an analog multiplier. This multiplies the received ultrasound signal with the signal from a master oscillator and measures the phase difference between the two input signals. The measurement cycle is repeated on the opposite direction and the phase measurements are subtracted to produce the phase shift between the upstream and downstream paths. The phase difference measured is then proportional to the volumetric flow at that point in time. A limitation of this phase detection method requires a long burst of ultrasound be transmitted from one transducer to the other, along the upstream or downstream path, with a duration long enough to allow the analog multiplier and the low pass filter time to settle on the phase value.

Crystal Biotech, Inc. (CBI) uses another method to measure phase shifts in a Transit Time flow meter created by Ronald Patton. CBI simultaneously transmits a short burst of ultrasound from two transducers in a probe and compares the phase shift of the received ultrasound bursts from the upstream and downstream paths directly to each other. The CBI Transmit Time flow meter includes a digital circuit with a single output. This output signal has its duty cycle modulated by the phase difference. This single modulated output switches on and off a current source with a capacitor as its load with a selectable number of pulses. The current source is switched on and off and the capacitor is used to store the charge, which is proportional to the time the current source is on. The charge on the capacitor generates a voltage, which is proportional to the phase shift between the two input signals. One shortcoming of the CBI device is that the portion of the signal representing the change in phase is a small percentage of the total charge on the capacitor. Therefore, it is difficult to reliably measure the small phase changes generated by the CBI Transit Time flow meter.

For the reasons stated above, and for other reasons stated below which will become apparent to those skilled in the art upon reading and understanding the present specification, there is a need in the art for a phase detector that provides a more rapid and accurate measure of the phase difference between two signals.

SUMMARY

The above mentioned problems with phase detectors and other problems are addressed by the present invention and will be understood by reading and studying the following specification. A phase detector is described which modulates the duty cycle of first and second output signals with a phase difference between the first and second input signals and uses the duty cycle modulated signals to create a differential signal that is proportional to the phase difference between the first and second input signals. For example, in one embodiment, the phase detector creates the differential voltage by charging first and second capacitors through switches controlled by the duty cycle modulated first and second output signals.

DETAILED DESCRIPTION

The following detailed description refers to the accompanying drawings which form a part of the specification. The drawings show, and the detailed description describes, by way of illustration specific illustrative embodiments in which the invention may be practiced. These embodiments are described in sufficient detail to enable those skilled in the art to practice the invention. Other embodiments may be used and logical, mechanical and electrical changes may be made without departing from the scope of the present invention. The following detailed description is, therefore, not to be taken in a limiting sense.

I. Overview

This detailed description provides a number of illustrative embodiments of a phase detector constructed according to the teachings of the present invention. These phase detectors generate a differential signal that is proportional to the phase difference between first and second input signals. The phase detectors can be used in any number of electronic circuits that monitor, process or determine the phase difference between first and second signals. For example, phase detectors constructed according to the teachings of the present invention can be used in phase lock loops in the communications arena. Further, phase detectors constructed according to the teachings of the present invention can also be used in the medical arts in devices such as transit time flow meters. Phase detectors constructed according to the teachings of the present invention can also be used in a wide variety of other electronic circuits and systems.

Sections II and III of this detailed description describe first and second embodiments of a phase detector that use duty cycle modulation of two signals to generate a differential output that is proportional to the phase difference between the two signals. Sections IV describes a third embodiment of a phase detector that uses first and second duty cycle modulated signals to charge capacitors to create a voltage that is proportional to the phase difference between the first and second signals. Sections V and VII describe embodiments of duty cycle modulation used in phase detectors according to the teachings of the present invention. Section VI describes an embodiment of a pulse selector circuit for a phase detector. Section VIII describes another embodiment of a second stage of a phase detector according to the teachings of the present invention. Section IX describes another embodiment of a first stage of a phase detector according to the teachings of the present invention. Sections X and XII describe embodiments of transit time flow meters using a phase detector with duty cycle modulation. Section XI describes a phase lock loop with a phase detector with duty cycle modulation.

II. First Embodiment of a Phase Detector

Figure 1:
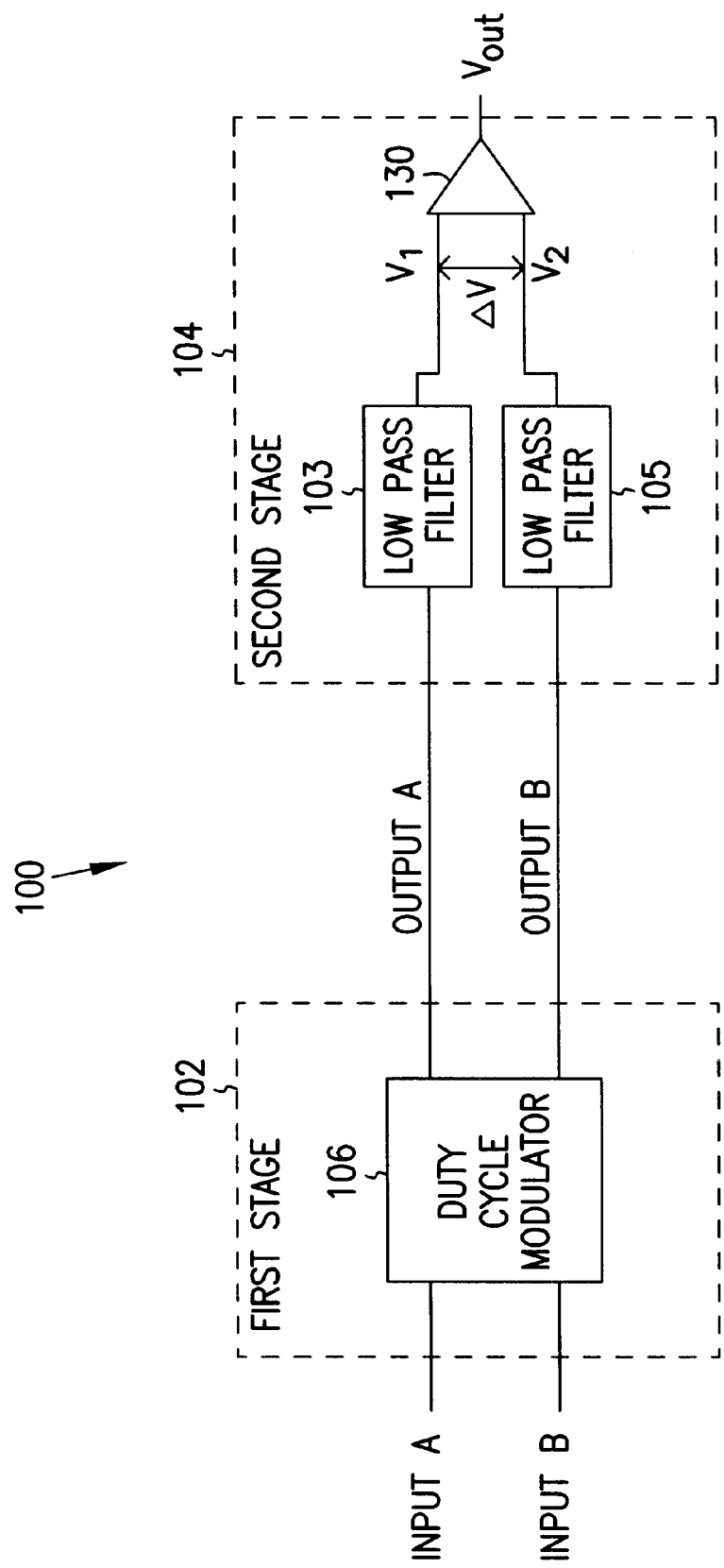
FIG. 1 is a block diagram of an embodiment of a phase detector constructed according to the teachings of the present invention.

FIG. 1 is a block diagram of an embodiment of a phase detector, indicated generally at 100, and constructed according to the teachings of the present invention. Phase detector 100 includes two stages: first stage 102 and second stage 104.

First stage 102 receives first and second input signals labeled INPUT A and INPUT B and produces first and second output signals labeled OUTPUT A and OUTPUT B. INPUT A and INPUT B each have a first duty cycle, e.g., a fifty percent or other fixed duty cycle. First stage 102 includes duty cycle modulator 106. Duty cycle modulator 106 modulates the duty cycles of OUTPUT A and OUTPUT B based on the phase difference between INPUT A and INPUT B. For example, the duty cycle of one of the first and second output signals is modified by increasing the duration of the high logic pulses of the signal by the phase difference between INPUT A and INPUT B. Meanwhile, the duty cycle of the other of the first and second output signals is modified by decreasing the duration of the high logic pulses of the signal by the phase difference between INPUT A and INPUT B.

Second stage 104 includes first and second low pass filters 103 and 105 that are coupled to receive OUTPUT A and OUTPUT B, respectively, from first stage 102. Low pass filters 103 and 105 generate signals $V_1$ and $V_2$ that are DC voltages that are proportional to the duration of the high logic levels for OUTPUT A and OUTPUT B, respectively. Thus, the difference between $V_1$ and $V_2$ is proportional to the phase difference between the input signals INPUT A and INPUT B since the only difference between the duty cycles of OUTPUT A and OUTPUT B was imposed by duty cycle modulator 106 based on the phases of INPUT A and INPUT B.

Second stage 104 also includes amplifier 130 that amplifies the difference between $V_1$ and $V_2$. This single ended signal, $V_{OUT}$, is proportional to the phase difference between INPUT A and INPUT B. In another embodiment, amplifier 130 is replaced with an analog to digital converter that provides a digital output signal for $V_{OUT}$. In a further embodiment, amplifier 130 is replaced with first and second analog to digital converters that provide signals $V_1$ and $V_2$ as digital outputs. In another embodiment, amplifier 130 is replaced with first and second analog to digital converters and a subtractor that provides an output signal, $V_{OUT}$, with the first analog to digital converter converting the signal $V_1$ and the second analog to digital converter converting the signal $V_2$. In other embodiments, amplifier 130 may be replaced with other appropriate circuitry used to process the analog outputs $V_1$ and $V_2$.

In operation, phase detector 100 detects the phase difference between INPUT A and INPUT B. Duty cycle modulator 106 receives INPUT A and INPUT B. Duty cycle modulator 106 adjusts the duty cycle of OUTPUT A increasing the duration of the high logic level pulses in OUTPUT A by a time substantially equal to the phase difference between INPUT A and INPUT B. Further, duty cycle modulator 106 also adjusts the duty cycle of OUTPUT B by decreasing the duration of the high logic level pulses of OUTPUT B by a time substantially equal to the phase difference between INPUT A and INPUT B.

Low pass filters 103 and 105 generate voltages $V_1$ and $V_2$, respectively, that are proportional to the duration of the high logic level pulses in OUTPUT A and OUTPUT B, respectively. Amplifier 130 amplifies the difference between $V_1$ and $V_2$ ($\Delta V$) to produce $V_{OUT}$. $V_{OUT}$ is proportional to the phase difference between INPUT A and INPUT B.

III. Second Embodiment of a Phase Detector

Figure 2:
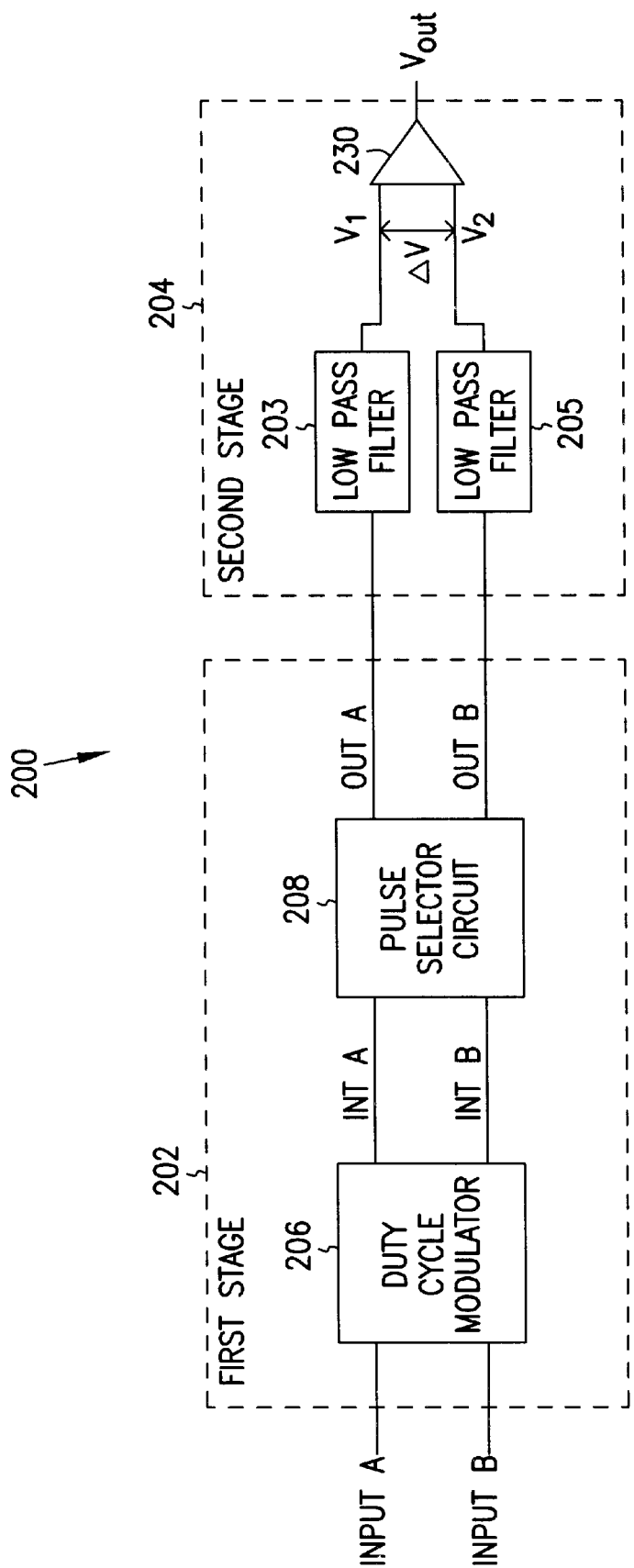
FIG. 2 is a block diagram of another embodiment of a phase detector constructed according to the teachings of the present invention.

FIG. 2 is a block diagram of an embodiment of a phase detector, indicated generally at 200, and constructed according to the teachings of the present invention. Phase detector 200 includes two stages: first stage 202 and second stage 204.

First stage 202 receives first and second input signals labeled INPUT A and INPUT B and produces first and second output signals labeled OUT A and OUT B. INPUT A and INPUT B each have a first duty cycle, e.g., a fifty percent or other fixed duty cycle. First stage 202 includes duty cycle modulator 206. Duty cycle modulator 206 modulates the duty cycles of INT A and INT B based on the phase difference between INPUT A and INPUT B. For example, the duty cycle of one of the INT A and INT B is modified by increasing the duration of the high logic pulses of the signal by the phase difference between INPUT A and INPUT B. Meanwhile, the duty cycle of the other of INT A and INT B is modified by decreasing the duration of the high logic pulses of the signal by the phase difference between INPUT A and INPUT B.

First stage 202 also includes pulse selector circuit 208. Pulse selector circuit 208 selects a number of pulses within the signals INT A and INT B to be provided as output signals OUT A and OUT B to second stage 204. Pulse selector circuit 208 may be programmable to select any appropriate number of pulses in INT A and INT B. Further, the selected pulses may begin with any appropriate pulse within signals INT A and INT B. For example, pulse selector 208 may select four pulses within a train of 10 pulses beginning with pulse number 3.

In the embodiment shown, pulse selector circuit 208 follows duty cycle modulator 206. However, it is understood that in other embodiments pulse selector circuit 208 precedes duty cycle modulator 206 or is incorporated into duty cycle modulator 206 such that pulses are selected and modulated by the same circuit.

Second stage 204 includes first and second low pass filters 203 and 205 that are coupled to receive OUT A and OUT B, respectively, from first stage 202. Low pass filters 203 and 205 generate signals $V_1$ and $V_2$ that are DC voltages that are proportional to the duration of the high logic levels for OUT A and OUT B, respectively. Thus, the difference between $V_1$ and $V_2$ ($\Delta V$) is proportional to the phase difference between the input signals INPUT A and INPUT B since the only difference between the duty cycles of OUT A and OUT B was imposed by duty cycle modulator 206 based on the phase difference between INPUT A and INPUT B.

Second stage 204 also includes amplifier 230 that amplifies the difference between $V_1$ and $V_2$ ($\Delta V$). This signal, $V_{OUT}$, is proportional to the phase difference between INPUT A and INPUT B. In one embodiment, amplifier 230 includes a sample and hold circuit that samples and holds the differential voltage, $\Delta V$, after pulses are passed by pulse selector circuit 208.

In operation, phase detector 200 detects the phase difference between INPUT A and INPUT B. Duty cycle modulator 206 receives INPUT A and INPUT B. Duty cycle modulator 206 adjusts the duty cycle of INT A by increasing the duration of the high logic level pulses in INT A by a time substantially equal to the phase difference between INPUT A and INPUT B. Further, duty cycle modulator 206 also adjusts the duty cycle of INT B by decreasing the duration of the high logic level pulses of INT B by a time substantially equal to the phase difference between INPUT A and INPUT B.

Pulse selector circuit 208 selects a number of pulses in INT A and INT B to provide to low pass filters 203 and 205, respectively.

Low pass filters 203 and 205 generate voltages $V_1$ and $V_2$, respectively, that are proportional to the duration of the high logic level pulses in OUT A and OUT B, respectively. Amplifier 230 amplifies the difference between $V_1$ and $V_2$ ($\Delta V$) to produce $V_{OUT}$. $V_{OUT}$ is proportional to the phase difference between INPUT A and INPUT B.

IV. Third Embodiment of Phase detector

Figure 3:
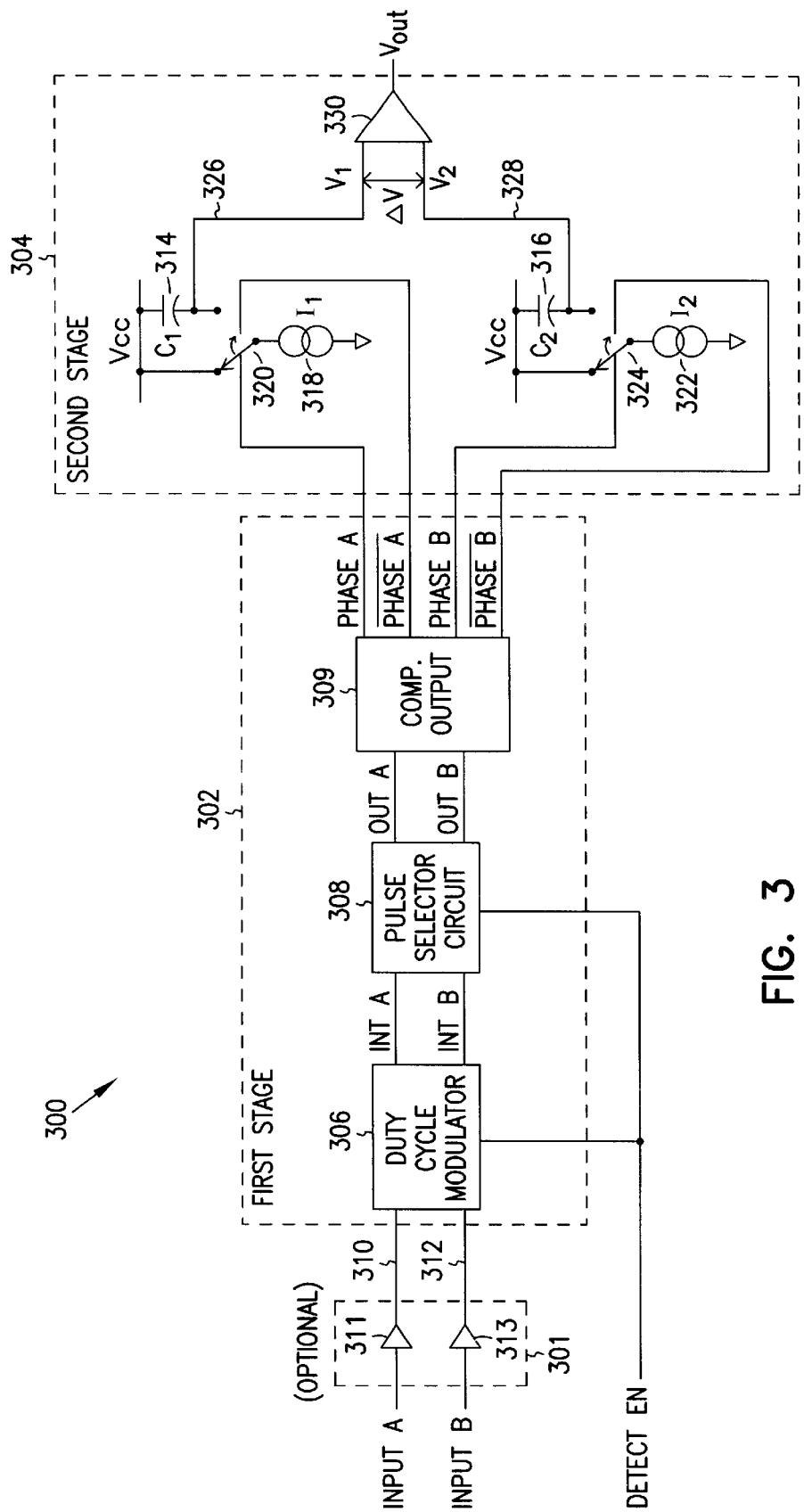
FIG. 3 is a block diagram of another embodiment of a phase detector constructed according to the teachings of the present invention.

FIG. 3 is a block diagram of an embodiment of a phase detector indicated generally at 300 and constructed according to the teachings of the present invention. Phase detector 300 measures the phase difference or time shift between two input signals, namely signals INPUT A and INPUT B.

As an overview, phase detector 300 includes first and second stages 302 and 304. First stage 302 uses duty cycle modulation to modulate the duty cycle of the output signals with the phase difference between INPUT A and INPUT B. First stage 302 further selects a number of pulses from the duty cycle modulated signals to be further processed by second stage 304.

Second stage 304 uses the duty cycle modulated signals from first stage 302 to control switches that charge first and second capacitors. Once charged, the voltages on the capacitors are related to the duty cycle of the duty cycle modulated signals. Since the duty cycles of the signals used to control the charging of the capacitors contain information about the phase difference between INPUT A and INPUT B, the voltages on the capacitors, once charged, provide a differential voltage output that is related to the phase difference between INPUT A and INPUT B. For example, in one embodiment, the differential voltage is proportional to twice the phase difference between INPUT A and INPUT B.

A. First Stage—Duty Cycle Modulation and Pulse Selection

First stage 302 operates on input signals labeled as INPUT A and INPUT B in FIG. 3. First stage 302 modulates the duty cycle of the output signals and selects a number of pulses from the duty cycle modulated signals for further processing. First stage 302 includes duty cycle modulator 306 and pulse selector circuit 308.

Duty cycle modulator 306 includes first and second inputs 310 and 312. Duty cycle modulator 306 is designed to process square wave inputs. Thus, in one embodiment, optional comparators 311 and 313 (collectively 301) are provided, when necessary, at inputs 310 and 312, respectively, to convert signals INPUT A and INPUT B to square wave format. For simplicity, the signals provided to duty cycle modulator 306 at inputs 310 and 312 are referred to as INPUT A and INPUT B whether or not comparators 301 are included.

Signals INPUT A and INPUT B are each periodic signals that have substantially the same frequency and the same nominal duty cycle, e.g., a fifty percent duty cycle. In one embodiment, the high logic level pulses ("the active period of the signal") in the respective square waves of signals INPUT A and INPUT B are substantially one half of the period of the signals INPUT A and INPUT B. INPUT A and INPUT B may, however, have different phase, e.g., INPUT A may be shifted in time with respect to INPUT B.

1. Duty Cycle Modulation

Duty cycle modulator 306 uses the phase difference between INPUT A and INPUT B, if any, to generate output signals labeled INT A and INT B. INT A and INT B have the same frequency as INPUT A and INPUT B but their duty cycles have been modulated from the nominal, e.g., fifty percent duty cycle, based on the phase difference between the signals INPUT A and INPUT B. For example, in one embodiment, the duration of the high logic level pulses in the signal INT A is increased by the duration of the phase difference between INPUT A and INPUT B and the duration of the high logic level pulses in the signal INT B is decreased by the same amount.

As described below with respect to FIGS. 6A through 6K, in one embodiment, signals INT A and INT B are created based on the rising and falling edges of signals INPUT A and INPUT B. Advantageously, the use of both rising and falling edges in performing phase modulation reduces problems with cross-over when signals INPUT A and INPUT B are close to phase alignment.

2. Pulse Selection

Pulse selector circuit 308 selects pulses from signals INT A and INT B to be used by second stage 304 to determine the phase difference between INPUT A and INPUT B. Pulse selector circuit 308 can be programmed as to the number of pulses to select and which pulses within the pulse trains of INT A and INT B to select. In one embodiment, pulse selector 308 essentially selects the pulses to be used by counting pulses after a time delay from the transmission of signals that created signals INPUT A and INPUT B. This selection can be based on data stored in a non-volatile memory associated with the pulse selector that downloads data for selected fixed time delays based on the operating environment of phase detector 300.

For example, in one embodiment, signals INPUT A and INPUT B comprise signals derived from 16 cycles of a 10 MHZ ultrasonic waveform used in a transit time flow meter. Pulse selector circuit 308 is programmed to select, e.g., the eighth pulse in each of the signals INT A and INT B. These pulses are used by second stage 304 to determine the phase difference between the signals INPUT A and INPUT B. Advantageously, these single pulses from the signals INT A and INT B provide sufficient information to provide a measure of the phase difference between the signals INPUT A and INPUT B. By using a small number of pulses, phase detector 300 can be used in low power implementations such as implanted medical devices.

Alternatively, pulse selector circuit 308 can select a larger number of specified pulses from the signals INT A and INT B, e.g., four pulses from the middle of the pulse train. In this case, second stage 304 advantageously averages the information on the phase difference for the four pulses to provide a measure of the phase difference detected by phase detector 300. In this manner, minor variations in phase difference from pulse-to-pulse are averaged out by second stage 304.

It is noted that pulses located near the middle of the pulse trains of signals INT A and INT B may provide a more accurate measure of the phase difference between INPUT A and INPUT B.

Pulse selector circuit 308 provides the selected pulses from INT A and INT B to complimentary output 309 as signals OUT A and OUT B to generate complementary outputs PHASE A, $\overline{\text{PHASE A}}$, PHASE B, and $\overline{\text{PHASE B}}$. These outputs are provided to second stage 304.

One embodiment of a pulse selector circuit is described below with respect to FIG. 3. The circuit of FIG. 3 is provided by way of example and not by way of limitation.

A signal labeled DETECT EN is also provided to both duty cycle modulator 306 and pulse selector circuit 308. The DETECT EN signal enables phase detector 300 to operate.

B. Second Stage—Generation of Voltage Related to Phase Difference

Second stage 304 uses the signals PHASE A, $\overline{\text{PHASE A}}$, PHASE B, and $\overline{\text{PHASE B}}$ from first stage 302 to create a voltage, labeled $V_{OUT}$, that is related to the phase difference between the signals INPUT A and INPUT B. Second stage 304 includes a pair of capacitors 314 and 316. Capacitor 314 is coupled to current source 318 through switch 320. Switch 320 is controlled based on the signals PHASE A and $\overline{\text{PHASE A}}$ from complementary output 309 of first stage 302. Similarly, capacitor 316 is coupled to current source 322 through switch 324. Switch 324 is controlled based on the signals PHASE B and $\overline{\text{PHASE B}}$ from complementary output 309 of first stage 302.

Capacitor 314 is coupled between a power supply, $V_{CC}$, and input 326 of amplifier 330. Similarly, capacitor 316 is coupled between a power supply, $V_{CC}$, and input 328 of amplifier 330. Amplifier 330 receives signals $V_1$ and $V_2$ and provides the output, $V_{OUT}$, for phase detector 300.

C. Operation

In operation, phase detector 300 receives signals INPUT A and INPUT B and determines the phase difference, if any, between the two signals. Initially, duty cycle modulator 306 creates signals INT A and INT B by modulating INT A and INT B based on the phase or phase difference between signals INPUT A and INPUT B. Pulse selector 308 then selects a number of pulses in the pulse trains of signals INT A and INT B and provides those pulses to complementary output 309 to generate signals PHASE A, $\overline{\text{PHASE A}}$, PHASE B, and $\overline{\text{PHASE B}}$ for second stage 304.

At second stage 304, signals PHASE A, $\overline{\text{PHASE A}}$, PHASE B, and $\overline{\text{PHASE B}}$ control the operation of switches 320 and 324, respectively. When the signal $\overline{\text{PHASE A}}$ is a high logic level, switch 320 couples current source 318 to capacitor 314. This causes the voltage at input 326 to decrease due to charging of capacitor 314. When the signal $\overline{\text{PHASE A}}$ is a low logic level, switch 320 decouples current source 318 from capacitor 314. Thus, capacitor 314 charges at a substantially constant rate during the high logic level pulse of $\overline{\text{PHASE A}}$ and does not charge when $\overline{\text{PHASE A}}$ is a low logic level.

Similarly, switch 324 couples capacitor 316 to current source 322 during the high logic pulses of signal $\overline{\text{PHASE B}}$ so as to charge capacitor 316 and reduce the voltage at input 328.

When the signals INPUT A and INPUT B are out of phase, the duty cycles of signals. $\overline{\text{PHASE A}}$ and $\overline{\text{PHASE B}}$ are different due to the effect of duty cycle modulator 306. Thus, the voltage at inputs 326 and 328 after application of signals $\overline{\text{PHASE A}}$ and $\overline{\text{PHASE B}}$ are also different. The difference in voltages at inputs 326 and 328, labeled $\Delta V$, is proportional to the phase difference between the signals INPUT A and INPUT B. Amplifier 330 amplifies this differential voltage and provides an the output $V_{OUT}$ as a measure of the phase difference.

The relationship between the differential voltage $\Delta V$ and the phase difference between signals INPUT A and INPUT B can be represented mathematically as follows. First, after application of signal $\overline{\text{PHASE A}}$ to second stage 304, the voltage at input 326 can be represented as shown in Equation 1.

$$V_1 = V_{CC} - n(1/2T + \Delta t)(i_1/c_1) \tag{1}$$

Figure 8:
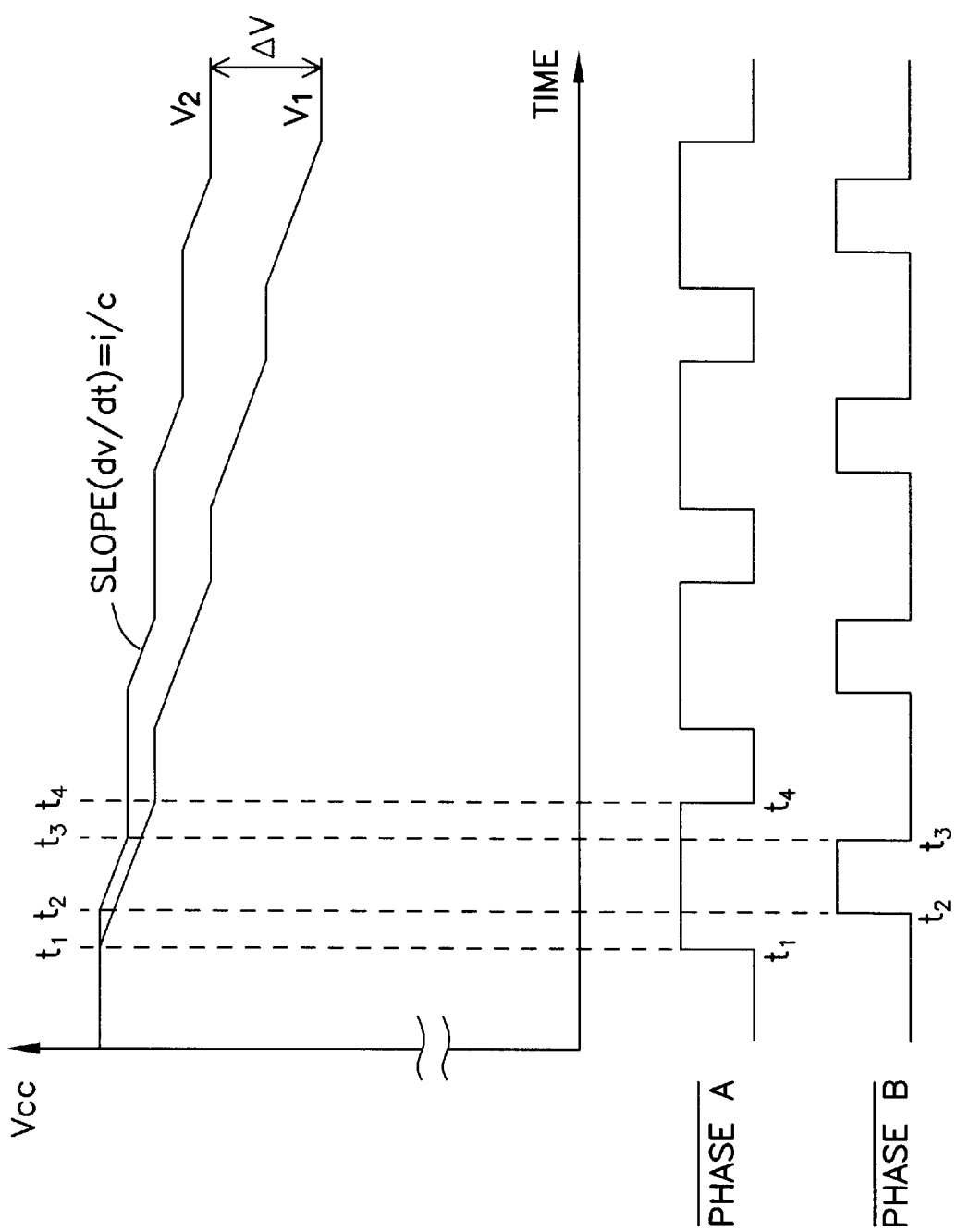
FIG. 8A is a graph that illustrates a differential output voltage of a phase detector over time according to the teachings of the present invention.
FIGS. 8B and 8C are graphs that illustrates duty cycle modulated signals according to the teachings of the present invention.

Equation 1 describes the fact that the voltage at input 326, $V_1$, starts out at a value of $V_{CC}$ before any high logic level pulses in the signal $\overline{\text{PHASE A}}$ are processed. Equation 1 further recognizes that for each of the n high logic level pulses of signal $\overline{\text{PHASE A}}$ processed by second stage 304, the voltage at input 326 decreases by a calculable amount due to the charging of capacitor 314 during each pulse. This is shown graphically in FIGS. 8A, 8B and 8C.

The change in the voltage on a capacitor is calculable beginning with the fundamental relationship shown in Equation 2:

$$dV/dt = i/c \tag{2}$$

To determine the change in voltage for a capacitor over a given period of time, Equation 2 can be rewritten as follows:

$$dV = (i/c)dt \tag{3}$$

In the context of second stage 304 of phase detector 300, the values for i and c are known and constant, namely $i_1$ and $c_1$. The value for the term dt represents the time that the signal $\overline{\text{PHASE A}}$ is at a high logic level. This time is approximately one half of the period (1/2 T in Equation 1) plus the phase difference in time between the signals INPUT A and INPUT B ($\Delta t$ in Equation 1) for the number of pulses (n).

Similarly, the voltage at input 328 can be represented by Equation 4:

$$V_2 = V_{CC} - n(1/2T - \Delta t)(i_2/c_2) \tag{4}$$

In Equation 4 it is assumed that the duration of the high logic pulses in signal $\overline{\text{PHASE B}}$ has been decreased by the phase difference, $\Delta t$, by duty cycle modulator 306.

Equation 5 defines the differential voltage, $\Delta V$, provided to inputs 326 and 328 of amplifier 330 in terms of the voltages $V_1$ and $V_2$.

$$\Delta V = V_1 - V_2 \tag{5}$$

Inserting the terms from Equations 1 and 4 into Equation 5 results in Equation 6:

$$\Delta V = n[(1/2T)(i_2/c_2 - i_1/c_1) + \Delta t(i_1/c_1 + i_2/c_2)] \tag{6}$$

If the currents $i_1$ and $i_2$ are assumed to be equal and the capacitances $c_1$ and $c_2$ are also considered to be equal, then Equation 6 can be reduced further to the following:

$$\Delta V = 2n\Delta t(i/c) \tag{7}$$

Thus, it can be seen that the differential voltage $\Delta V$ is proportional to the phase difference ($\Delta t$). Advantageously, the differential voltage is also independent of the supply voltage $V_{CC}$. Further, the differential voltage has an inherent gain of two.

When more than one pulse of the signals $\overline{\text{PHASE A}}$ and $\overline{\text{PHASE B}}$ are used, Equation 7 shows that the differential voltage advantageously performs an averaging function for the phase difference modulated on each pulse of the signals $\overline{\text{PHASE A}}$ and $\overline{\text{PHASE B}}$.

Several factors may be considered in selecting values for the capacitors and currents of second stage 304. For example, errors in the output of phase detector 300 can be reduced by setting the current from current sources 318 and 322 to substantially the same current level and by setting the capacitance of capacitors $C_1$ and $C_2$ at substantially the same level. Further, the number of cycles in signals $\overline{\text{PHASE A}}$ and $\overline{\text{PHASE B}}$ should be considered in combination with the capacitances and currents of second stage 304 to assure sufficient voltage at inputs 326 and 328 to allow current sources 318 and 322 to function properly.

In some embodiments, current sources 318 and 322 are fabricated as current mirrors. In these embodiments, a resistance may be coupled to the emitters of the transistors in the current mirror (e.g., current mirrors 718 and 722 in FIG. 7) to reduce the susceptibility of second stage 304 to changes in temperature and differences in base-emitter voltage differences from transistor to transistor. Further, a current mirror can be driven by a fixed reference voltage to reduce changes caused by fluctuations in $V_{CC}$. In other embodiments, a common current mirror having multiple legs is used to implement current sources 318 and 322. Further, in other embodiments, circuits other than a current mirror can be used to provide the current to charge capacitors 314 and 316.

V. Duty Cycle Modulator

Figure 4:
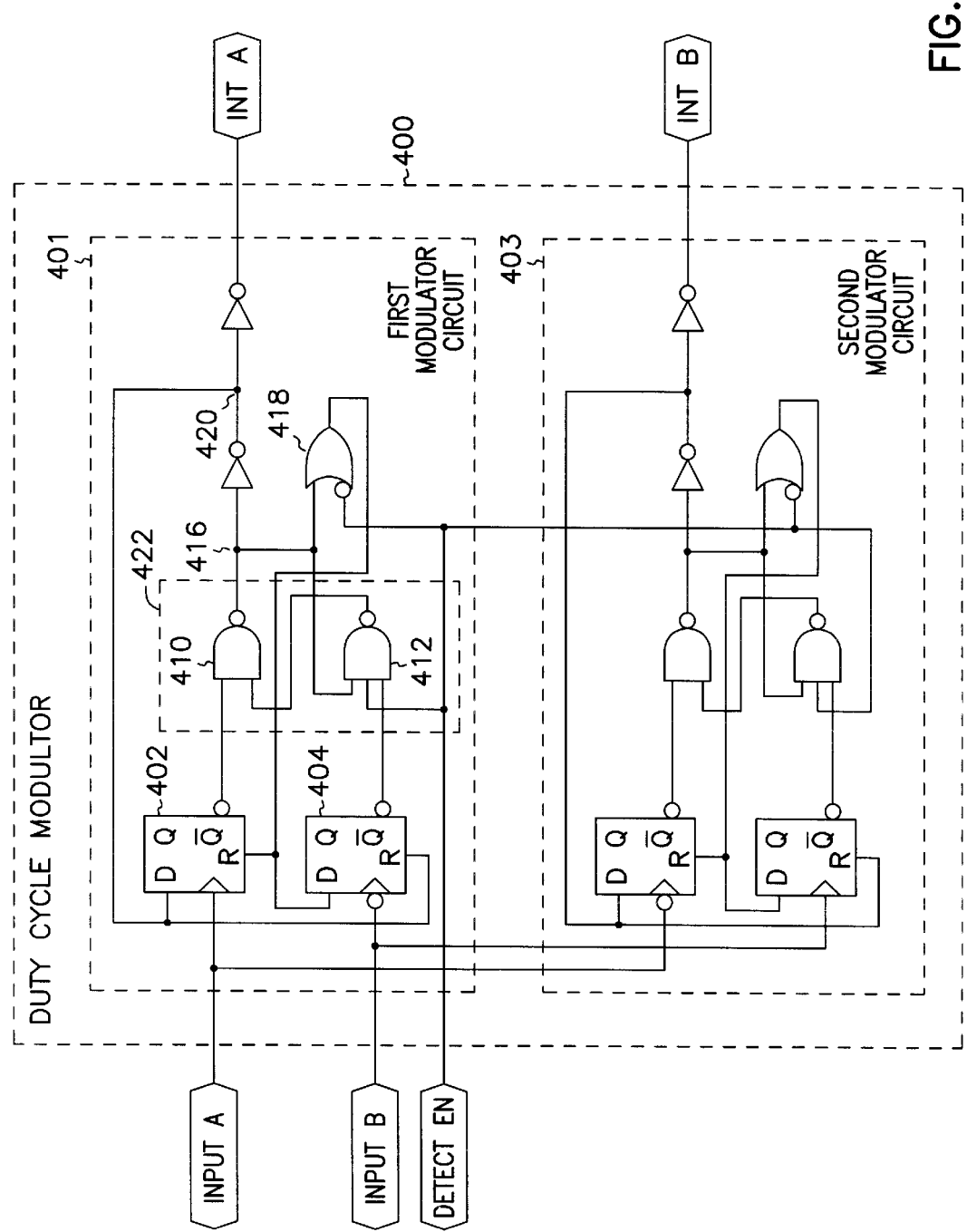
FIG. 4 is a schematic diagram of an embodiment of a stage of a phase detector that modulates the duty cycle of first and second output signals according to the teachings of the present invention.

FIG. 4 is a schematic diagram of an embodiment of a duty cycle modulator circuit, indicated generally at 400, and constructed according to the teachings of the present invention. Circuit 400 creates duty cycle modulated signals INT A and INT B based on input signals INPUT A and INPUT B. Circuit 400 includes first and second modulator circuits 401 and 403. Essentially circuits 401 and 403 create signals INT A and INT B by triggering off the rising edge of one of the input signals and the falling edge of the other input signal. Specifically, circuit 401 creates the signal INT A by triggering off the rising edge of INPUT A and the falling edge of INPUT B. Additionally, circuit 403 creates the signal INT B by triggering off the rising edge of INPUT B and the falling edge of INPUT A. For simplicity of the description, only circuit 401 is described in detail. It is understood that circuit 403 functions in the same or similar manner.

Circuit 401 includes first and second flip-flops 402 and 404. INPUT A is provided to the clock input of flip-flop 402 and the inverse of INPUT B is provided to the clock input of flip-flop 404. Circuit 401 also includes first and second NAND gates 410 and 412. NAND gates 410 and 412 are coupled to form flip-flop 422 with one input coupled to the $\overline{Q}$ output of flip-flop 402 and another input coupled to the $\overline{Q}$ output of flip-flop 404. The output of NAND gate 410 at node 416 is coupled through two inverters to provide the output INT A.

Circuit 401 also includes OR gate 418. OR gate 418 is coupled to the output of NAND gate 410 and also to the complement of the enablement signal, DETECT EN. DETECT EN is also provided as a clear input to the flip-flop 422 formed by NAND gates 410 and 412.

In operation, circuit 401 creates the duty cycle modulated INT A signal from the signals INPUT A and INPUT B with pulses that begin on the positive edge of pulses in the INPUT A signal and end on the negative edge of pulses in the INPUT B signal. Initially, the DETECT EN signal has a low logic value. Thus, OR gate 418 produces a high logic signal that holds flip-flop 402 in reset. Further, node 420 is a high logic value, it holds flip-flop 404 in reset. Thus, both flip-flops 402 and 404 output high logic levels on their $\overline{Q}$ outputs. Flip-flop 422 is held in reset by the DETECT EN signal.

The creation of duty cycle modulation signal INT A begins by raising the DETECT EN signal to a high logic level. This releases flip-flop 422 from reset. Further, this changes the output of OR gate 418 to depend on the voltage at node 416. At this point the voltage on node 416 is low, so flip-flop 402 is also released from reset.

On a positive edge of a pulse from INPUT A, flip-flop 402 is set so its $\overline{Q}$ output becomes a low logic level. This change in state of flip-flop 402 sets flip-flop 422 such that node 416 transitions to a high logic level as does the output INT A. The voltage at node 420 transitions to a low logic level thereby releasing flip-flop 404 from reset. The output of OR gate 418 also changes back to a high logic level so as to reset flip-flop 402.

On a negative edge of a pulse in INPUT B, flip-flop 404 is set such that $\overline{Q}$ assumes a low logic level. This clears flip-flop 422 such that node 416 returns to a low logic level. The output signal INT A also returns to a low logic level. Thus, circuit 401 creates an output signal, INT A, with a duty cycle that is modulated with the phase difference between INPUT A and INPUT B by creating high logic pulses in INT A that begin with the leading edge of pulses in INPUT A and end with trailing edges of high logic pulses in INPUT B. Circuit 403 works in a similar manner to provide INT B with high logic pulses that begin with the leading edge of INPUT B and end with the trailing edge of INPUT A.

VI. Pulse Selector

Figure 5:
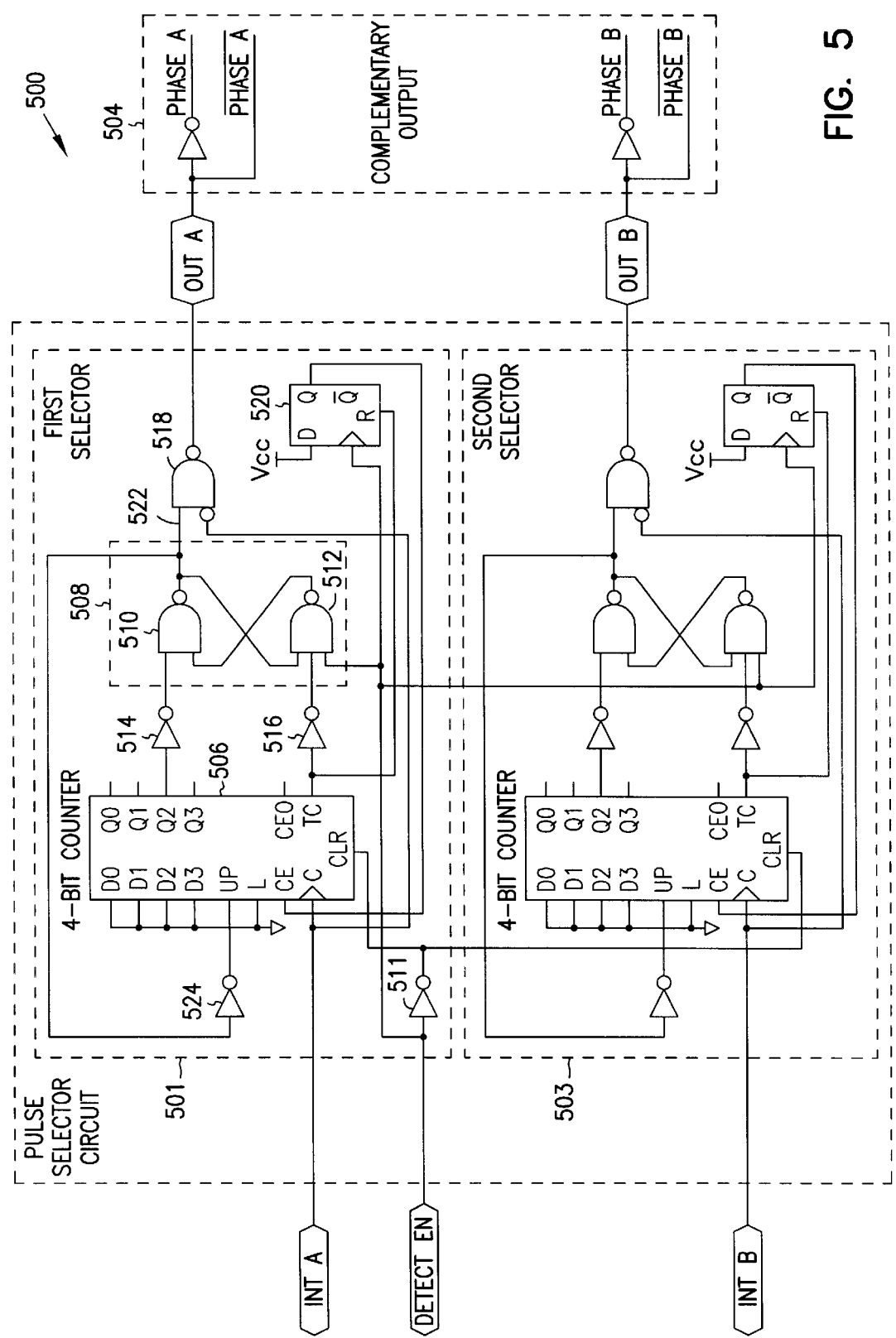
FIG. 5 is a schematic diagram of an embodiment of a stage of a phase detector that selects a number of pulses in first and second, duty cycle modulated signals according to the teachings of the present invention.
Figure 6:
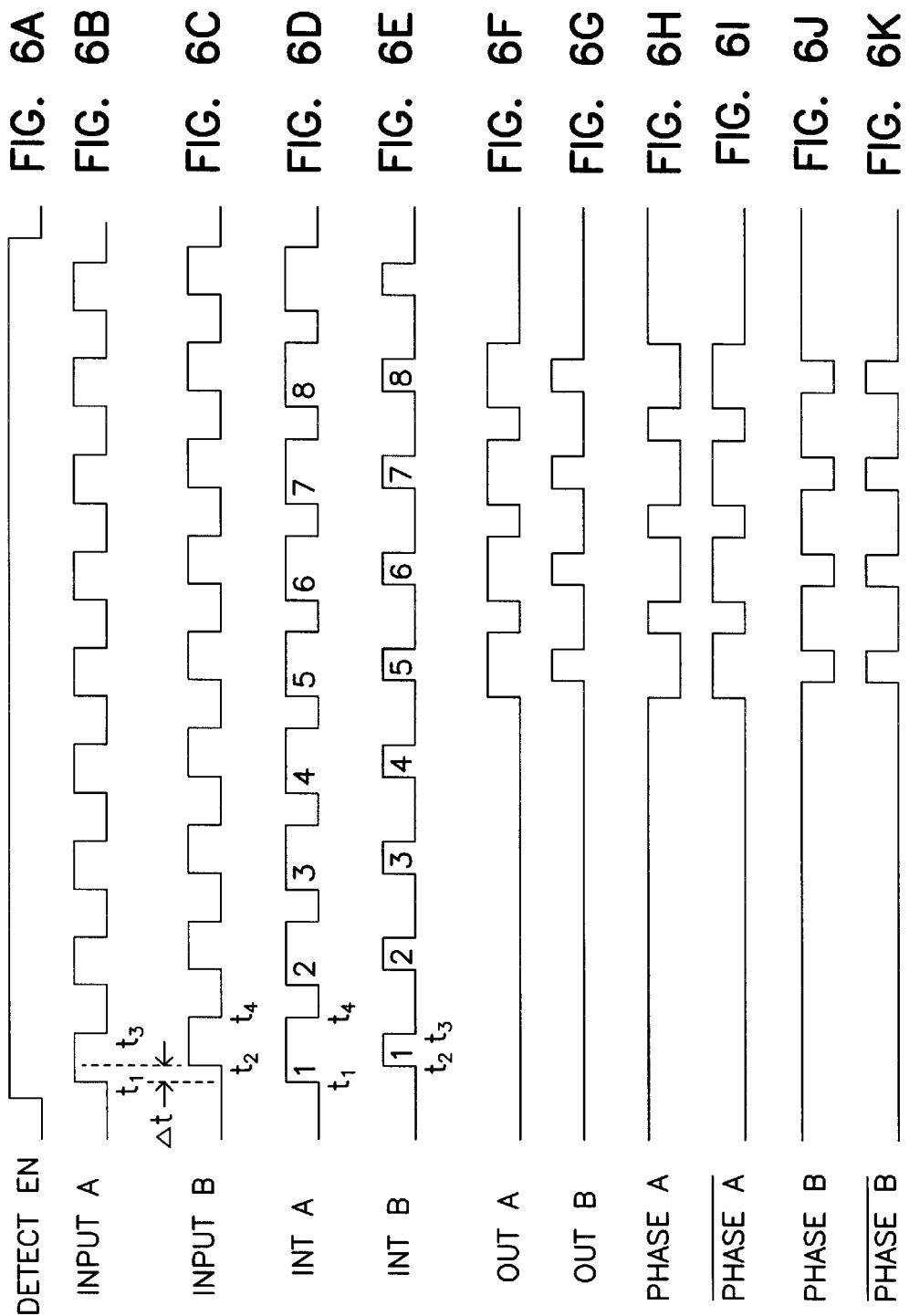
FIGS. 6A through 6K are timing diagrams that illustrate one embodiment of a process for modulating the duty cycle of first and second output signals according to the teachings of the present invention.

FIG. 5 is a schematic diagram of an embodiment of a pulse selector circuit, indicated generally at 500 and constructed according to the teachings of the present invention. Circuit 500 includes first and second selectors 501 and 503. First selector 501 selects a number of pulses in signal INT A. Second selector 503 selects a number of pulses in INT B. The outputs of first and second selectors 501 and 503 are provided to complementary output 504 to provide complementary output signals PHASE A, $\overline{\text{PHASE A}}$, PHASE B, and $\overline{\text{PHASE B}}$. Due to the similarities between first and second selectors 501 and 503, only first selector 501 is described in detail here. It is understood that second selector 503 operates in a similar manner.

First selector 501 includes a four bit, up-down counter 506. The clock input of counter 506 is coupled to receive the signal INT A. Additionally, the clear or reset input to counter 506 is coupled through inverter 511 to receive the enablement signal DETECT EN. In one embodiment, counter 506 is programmable counter with a four bit input (D0–D3) set to ground.

First selector 501 also includes flip-flop 508 formed from NAND gates 510 and 512. In one embodiment, one input of flip-flop 508 is coupled to the Q2 (third bit) output of counter 506 through inverter 514. Additionally, another input of flip-flop 508 is coupled from the terminal count (TC) output of counter 506 through inverter 516. A final input to flip-flop 508 is coupled to receive the DETECT EN signal.

First selector 501 also includes NAND gate 518 which creates an output labeled OUT A for first selector 501. NAND gate 518 receives the complement of signal INT A and a first output of flip-flop 508 at node 522. Node 522 is also provided as a feedback signal to the UP input of counter 506 through inverter 524.

Finally, first selector 501 includes a latch 520 that enables the operation of counter 506. The Q output of latch 520 is coupled to the count enable (CE) input of counter 506. Latch 520 also includes a reset input that is coupled to the TC output of counter 506. Finally, the clock input of latch 520 is coupled to the DETECT EN signal.

In operation, first selector 501 selects a number of pulses in signal INT A to pass through as signal OUT A. In this embodiment, first selector 501 is configured to select the second four pulses in INT A. It is understood that first selector 501 can be modified to select other pulses in INT A.

Initially, DETECT EN is at a low logic level. Thus, inverter 511 applies a high logic level to clear counter 506. Additionally, the low logic level of DETECT EN holds flip-flop 508 in a reset state with node 522 at a low logic level. This assures that OUT A is held at a high logic level prior to enabling the phase detector.

When the phase detector is enabled, first selector 501 receives a high logic level input on the DETECT EN signal. This applies a low logic signal to the clear input of counter 506 placing it in a condition to count up from zero. Further, latch 520 is set and provides a high logic input to the CE input of counter 506 thereby enabling counter 506. The high logic value for the DETECT EN signal also releases flip-flop 508 from being held in reset.

Counter 506 begins counting on the first leading edge of a pulse in input signal INT A after DETECT EN goes high. On each pulse in INT A, counter 506 increases as exhibited by signals Q0–Q3. With the first three pulses, there is no change in the output of NAND gate 518 since neither Q0 nor Q1 are coupled to provide output for counter 506. Thus, OUT A remains at a high logic level during the first three pulses.

When counter 506 reaches a value of four, Q2 transitions to a high logic value and inverter 514 provides a low logic level input to flip-flop 508. This drives node 522 to a high logic level. With node 522 at a high logic level, NAND gate 518 is allowed to pass the signal INT A as the output OUT A. Essentially, counter 506 counted the number of pulses in INT A to skip for pulse selector 500.

The high logic level at node 522 also provides a feedback signal to input UP of counter 506 through inverter 524. This signal indicates that counter 506 is to count down from its current value. Essentially, counter 506 now allows the next four pulses of INT A to be passed out as pulses in signal OUT A.

When counter 506 reaches zero, output TC is raised to a high logic level and resets flip-flop 508. The TC signal also clears latch 520 so as to disable counter 506 from counting. At this point, the output signal OUT A is at a high logic level until the next time DETECT EN is raised to a high logic level. Thus, selector 501 uses a four bit counter to select the second four pulses in the input signal INT A to provide as the output signal OUT A. Second selector 503 operates in a similar fashion for creating signal OUT B from signal INT B.

VII. Duty Cycle Modulation and Pulse Selection

FIGS. 6A through 6K are timing diagrams of an illustrative embodiment of a process for modulating the duty cycle of signals and selection of pulses by a phase detector according to the teachings of the present invention. This process is described in terms of phase detector 300 of FIG. 3. However, it is understood that the teachings of this process can be applied to other embodiments of phase detectors constructed according to the teachings of the present invention.

Phase detector 300 is enabled by a signal labeled DETECT EN. FIG. 6A illustrates an exemplary embodiment of signal DETECT EN. This signal enables the operation of duty cycle modulator 306 and pulse selector circuit 308.

FIGS. 6B and 6C illustrate exemplary signals for signals INPUT A and INPUT B provided to phase detector 300. In this example, signals INPUT A and INPUT B each include nine pulses and each have approximately a fifty percent duty cycle. There is a phase difference, denoted $\Delta t$ on FIGS. 6B, between signals INPUT A and INPUT B. The phase difference represents the difference in time between the beginning of corresponding pulses of INPUT A and INPUT B. For example, the first pulse in INPUT A begins at time $t_1$ and the first pulse in INPUT B begins at time $t_2$.

FIGS. 6D and 6E are timing diagrams that illustrate phase modulated signals INT A and INT B, respectively, created by duty cycle modulator 306. Duty cycle modulator 306 adds the phase difference $\Delta t$ to the high logic pulses of signal INPUT A to produce the signal INT A. Duty cycle modulator 306 initiates a high logic level pulse of INT A on the rising edge of INPUT A, e.g., at time $t_1$, and returns INT A to a low logic level on a falling edge of INPUT B, e.g., at time $t_4$. In practice, the complement of INPUT B can be used such that INT A rises on the rising edge of INPUT A and falls on the rising edge of the complement of INPUT B.

Duty cycle modulator 306 subtracts the phase difference $\Delta t$ from the high logic level pulses of INPUT B to produce INT B. Duty cycle modulator 306 initiates a high logic level pulse of INT B on a rising edge of INPUT B (or a falling edge of the complement of INPUT B), e.g., at time $t_2$, and returns INT B to a low logic level based on a falling edge of INPUT A, e.g., at time $t_3$. Thus, the signals INT A and INT B have duty cycles that are modulated based on the phase or the phase difference between INPUT A and INPUT B.

FIGS. 6F and 6G illustrate exemplary signals OUT A and OUT B, respectively, for first stage 302 of phase detector 300. In this embodiment, pulse selector circuit 308 is programmed to pass pulses five through eight of signals INT A and INT B.

FIGS. 6H, 6I, 6J, and 6K illustrate exemplary outputs from complementary output 309 of first stage 302. These outputs are PHASE A, $\overline{\text{PHASE A}}$, PHASE B, and $\overline{\text{PHASE B}}$ and are used to control the operation of second stage 304.

It is understood that the example shown here in FIGS. 6A through 6K are provided by way of illustration and not by way of limitation. For example, in some embodiments, INPUT A and INPUT B have a larger or smaller number of pulses. Also, in other embodiments, INPUT A and INPUT B each provide continuous input to first stage 302. Further, in other embodiments, signals PHASE A, $\overline{\text{PHASE A}}$, PHASE B, and $\overline{\text{PHASE B}}$ include a larger or smaller sampling of pulses from signals INT A and INT B. The number of pulses selected in signals PHASE A, $\overline{\text{PHASE A}}$, PHASE B, and $\overline{\text{PHASE B}}$ also varies with the application of the phase detector.

VIII. Another Embodiment of a Second Stage

Figure 7:
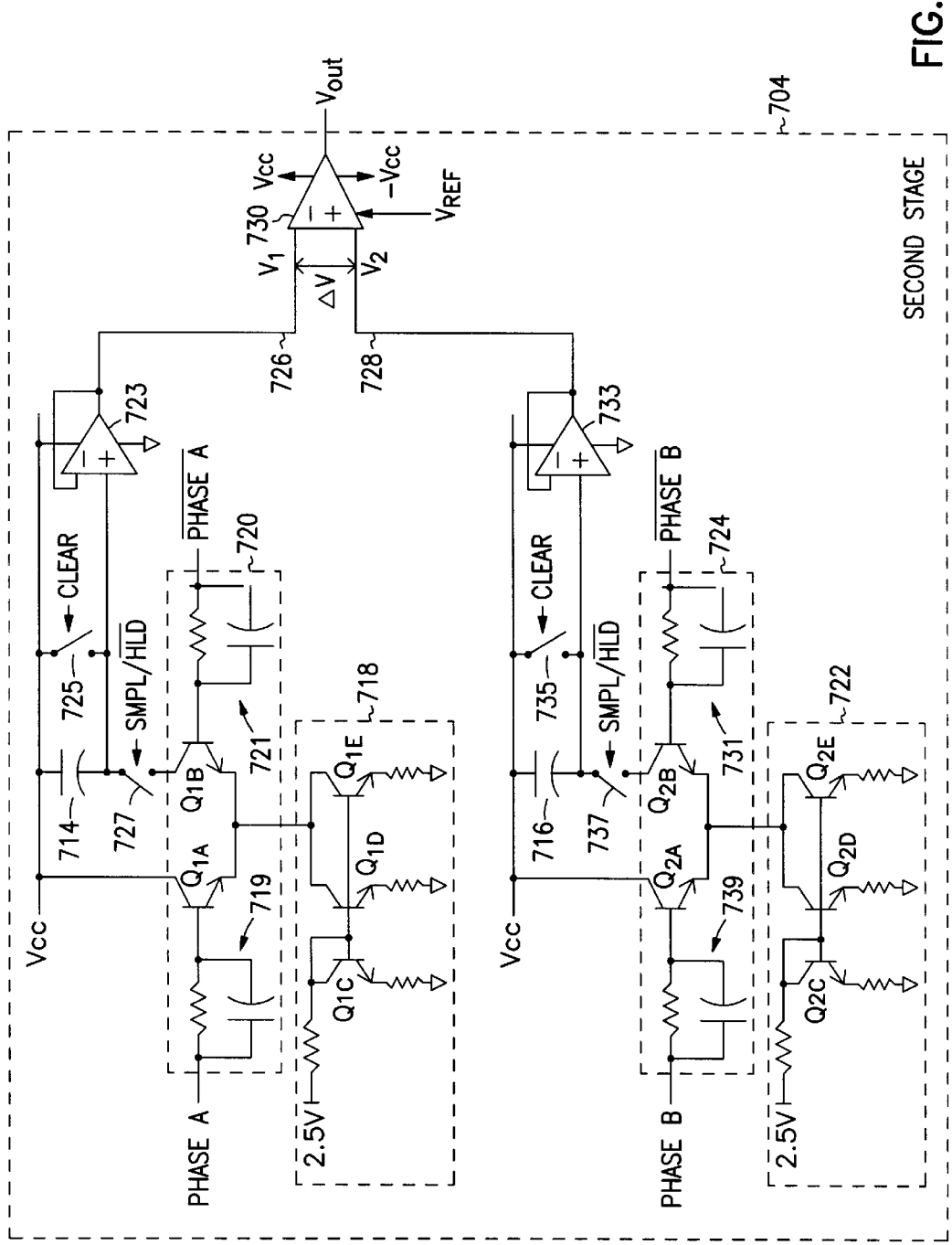
FIG. 7 is a schematic diagram of an embodiment of a switched current source used to charge a capacitor based on the duty cycle of an input signal according to the teachings of the present invention.

FIG. 7 is a schematic diagram of another embodiment of a second stage, indicated generally at 704, for use in a phase detector according to the teachings of the present invention. Second stage 704 uses signals PHASE A, $\overline{\text{PHASE A}}$, PHASE B and $\overline{\text{PHASE B}}$ from, for example, first stage 302 of FIG. 3 to create a voltage, labeled $V_{OUT}$. The voltage, $V_{OUT}$, is related to the phase difference between the signals INPUT A and INPUT B.

Second stage 704 includes a pair of capacitors 714 and 716. Capacitor 714 is coupled to current source 718 through switch 720. Capacitor 714 is coupled to input 726 of instrumentation amplifier 730 through buffer 723.

In this embodiment, current source 718 includes transistors $Q_{1C}$, $Q_{1D}$, $Q_{1E}$ that are coupled to form a current mirror. Optional resistors are coupled to the emitters of transistors $Q_{1C}$, $Q_{1D}$, $Q_{1E}$ to provide invariance to temperature change and to variations in emitter-base voltage. It is noted that the current mirror in this embodiment uses a 2.5 volt reference voltage to create the constant current for switch 720. Advantageously, this reference voltage reduces changes caused by fluctuations in the power supply $V_{CC}$. It is also noted that the value of the reference voltage in FIG. 7 can be varied as necessary for a particular application. The values shown are provided by way of illustration and not by way of limitation.

Switch 720 comprises a differential amplifier formed from transistors $Q_{1A}$ and $Q_{1B}$. Transistors $Q_{1B}$ and $Q_{1B}$ may be formed on the same die, e.g., using transistor arrays, to reduce differences in the emitter-base voltage due to temperature and other factors. Further, transistors $Q_{1A}$ and $Q_{1B}$ should be fast enough to allow even small phase differences on the order of 0.1 nanoseconds or less to be resolved.

The signal PHASE A is provided to a gate of transistor $Q_{1A}$ through an RC network 719. The signal $\overline{\text{PHASE A}}$ is provided to a gate of transistor $Q_{1B}$ through RC network 721.

Second stage 704 also includes switch 725 to clear the voltage on capacitor 714. Switch 725 is coupled in parallel with capacitor 714 and comprises, for example, an analog switch with a control input coupled to a signal labeled CLEAR. When the signal CLEAR is raised to a high voltage level, switch 725 is closed so as to clear the voltage on capacitor 714. Otherwise, the CLEAR signal is maintained at a low level to allow the voltage on capacitor 714 to be changed based on the signals PHASE A and $\overline{\text{PHASE A}}$.

Second stage 704 also includes switch 727 that allows the voltage on capacitor 714 to be held at a level so that the output of amplifier 730 can be read. Since switch 720 is formed with bipolar junction transistors, switch 720 would draw a small current even when the switch is off. Thus, switch 727 is added to prevent leakage from capacitor 714 that would destroy the integrity of the value stored on capacitor 714.

Capacitor 716 is coupled to current source 722 through switch 724. Capacitor 716 is coupled to input 728 of instrumentation amplifier 730 through buffer 733.

In this embodiment, current source 722 includes transistors $Q_{2C}$, $Q_{2D}$, $Q_{2E}$ that are coupled to form a current mirror. Optional resistors are coupled to the emitters of transistors $Q_{2C}$, $Q_{2D}$, $Q_{2E}$ to provide invariance to temperature change and to variations in emitter-base voltage. It is noted that the current mirror in this embodiment uses a 2.5 volt reference voltage to create the constant current for switch 724. Advantageously, this reference voltage reduces changes caused by fluctuations in the power supply $V_{CC}$. It is also noted that the value of the reference voltage and the value of the resistors shown in FIG. 7 can be varied as necessary for a particular application.

Current sources 722 and 718 may be matched current sources so as to provide substantially the same current for capacitors 714 and 716. Further, capacitors 714 and 716 may have substantially the same value.

Switch 724 comprises a differential amplifier formed from transistors $Q_{2A}$ and $Q_{2B}$. Transistors $Q_{2A}$ and $Q_{2B}$ may be formed on the same die, e.g., using transistor arrays, to reduce differences in the emitter-base voltage due to temperature and other factors. Further, transistors $Q_{2A}$ and $Q_{2B}$ should be fast enough to allow even small phase differences on the order of 0.1 nanoseconds or less to be resolved.

The signal PHASE B is provided to a gate of transistor $Q_{2A}$ through an RC network 739. The signal $\overline{\text{PHASE B}}$ is provided to a gate of transistor $Q_{2B}$ through RC network 731.

Second stage 704 also includes switch 735 to clear the voltage on capacitor 716. Switch 735 is coupled in parallel with capacitor 716 and comprises, for example, an analog switch with a control input coupled to a signal labeled CLEAR. When the signal CLEAR is raised to a high voltage level, switch 735 is closed so as to clear the voltage on capacitor 716. Otherwise, the CLEAR signal is maintained at a low level to allow the voltage on capacitor 716 to be changed based on the signals PHASE B and $\overline{\text{PHASE B}}$.

Second stage 704 also includes switch 737 that allows the voltage on capacitor 716 to be held at a level so that the output of amplifier 730 can be read.

Stray capacitance and leakage current should be reduced at the junction of capacitors 714 and 716 with the collectors of transistors $Q_{1B}$ and $Q_{2B}$ since the voltage on these capacitors directly affects the measurement of the phase difference by second stage 704. This includes the capacitance on the input to switches 720 and 724.

In operation, second stage 704 generates a signal, $V_{OUT}$, that is proportional to the phase difference between signals INPUT A and INPUT B of FIG. 3. Second stage 704 receives signals PHASE A, $\overline{\text{PHASE A}}$, PHASE B and $\overline{\text{PHASE B}}$ at switches 720 and 724. When the signal $\overline{\text{PHASE A}}$ is a high logic level, switch 720 couples current source 718 to capacitor 714. This causes the voltage at input 726 to decrease due to charging of capacitor 714. When the signal $\overline{\text{PHASE A}}$ is a low logic level, switch 720 decouples current source 718 from capacitor 714. Thus, capacitor 714 charges at a substantially constant rate during the high logic level pulse of $\overline{\text{PHASE A}}$ and does not charge when $\overline{\text{PHASE A}}$ is a low logic level.

Similarly, switch 724 couples capacitor 716 to current source 722 during the high logic pulses of signal $\overline{\text{PHASE B}}$ so as to charge capacitor 716 and reduce the voltage at input 728. When the signals INPUT A and INPUT B are out of phase, the duty cycles of signals $\overline{\text{PHASE A}}$ and $\overline{\text{PHASE B}}$ are different due to the effect of duty cycle modulator 306. Thus, the voltage at inputs 726 and 728 after application of signals $\overline{\text{PHASE A}}$ and $\overline{\text{PHASE B}}$ are also different. The difference in voltages at inputs 726 and 728, labeled ΔV, is proportional to the phase difference between the signals INPUT A and INPUT B. Amplifier 730 amplifies this differential voltage and provides an the output $V_{OUT}$ as a measure of the phase difference. The voltage $V_{OUT}$ is represented mathematically in Equation 8:

$$V_{OUT}=A\Delta V+V_{REF} \qquad (8)$$

wherein A is the gain of amplifier 730, ΔV is the differential voltage applied to amplifier 730, and $V_{REF}$ is an offset voltage applied to amplifier 730. The equation for ΔV is found above in Equation 6.

IX. Another Embodiment of a First Stage

Figure 9:
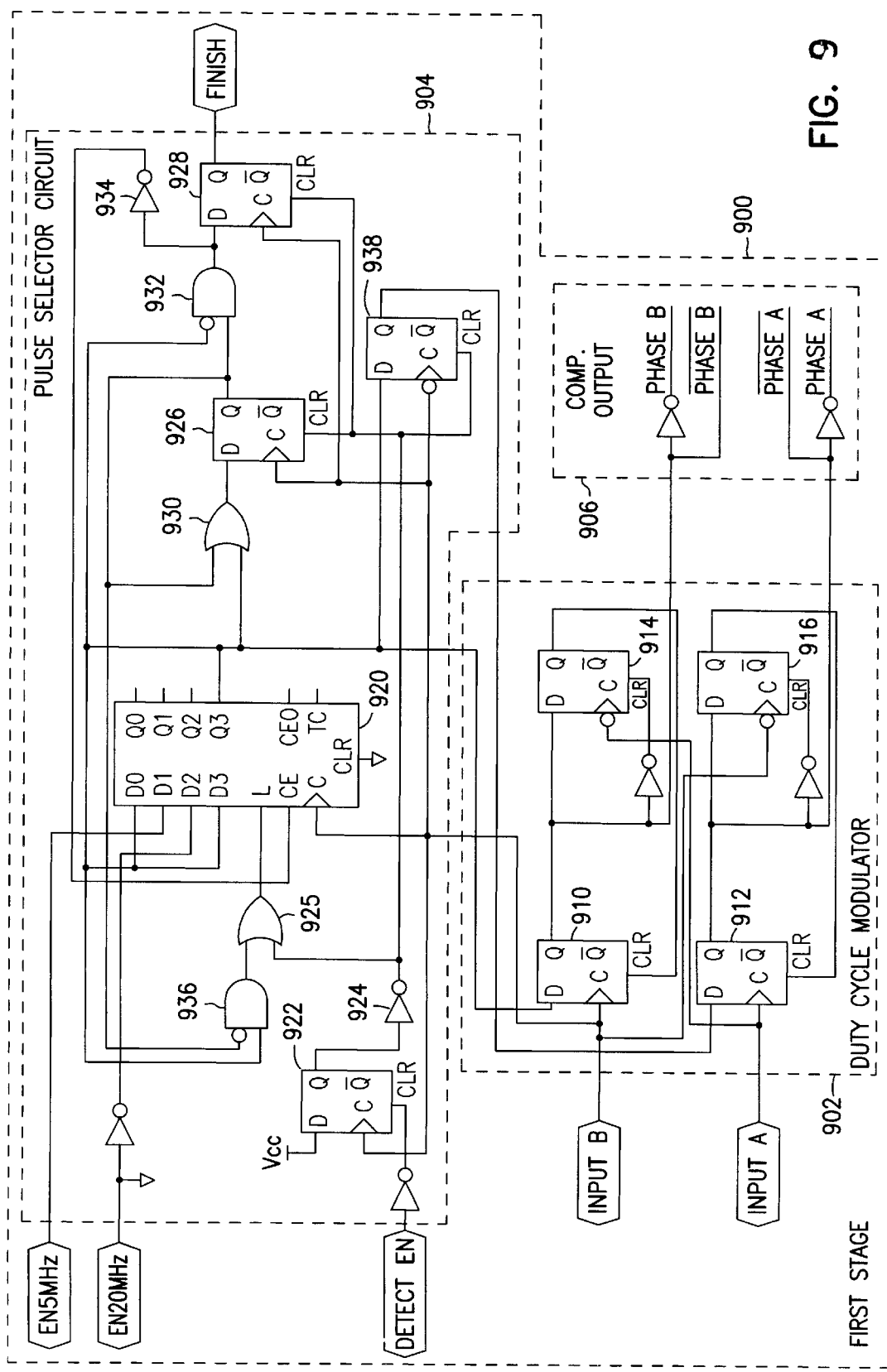
FIG. 9 is a schematic diagram of another embodiment of a first stage of a phase detector constructed according to the teachings of the present invention.

FIG. 9 is a schematic diagram of another embodiment of a first stage of a phase detector, indicated generally at 900, and constructed according to the teachings of the present invention. First stage 900 includes duty cycle modulator 902, pulse selector circuit 904 and complementary outputs 906. Duty cycle modulator 902 and pulse selector circuit 904 are described in turn below. In this embodiment, duty cycle modulator 902 only modulates the duty cycle of pulses in INPUT A and INPUT B for pulses that are selected by selector circuit 904.

A. Duty Cycle Modulator

Duty cycle modulator 902 includes flip-flops 910, 912, 914, and 916. Flip-flops 910 and 916 are triggered on INPUT B. Similarly, flip-flops 912 and 914 are triggered by INPUT A. Specifically, flip-flops 910 and 912 are triggered on the rising edges of INPUT B and INPUT A, respectively. Further, flip-flops 914 and 916 are triggered on the falling edges of INPUT A and INPUT B, respectively. Flip-flops 914 and 916 are set to be cleared by the inverse of the outputs of flip-flops 910 and 912, respectively. Similarly, flip-flops 910 and 912 are coupled to be cleared by the outputs of flip-flops 914 and 916, respectively. The outputs of flip-flops 910 and 912 comprise the outputs $\overline{\text{PHASE A}}$ and $\overline{\text{PHASE B}}$ of complementary outputs 906.

$\overline{\text{PHASE A}}$ and $\overline{\text{PHASE B}}$ are each generated in a similar manner. Therefore, for simplicity, only the output $\overline{\text{PHASE B}}$ is described in detail here. Initially, the signal DETECT EN transitions from a low logic level to a high logic level. This initiates the operation of pulse selector circuit 904. Pulse selector circuit 904 counts a selected number of pulses in INPUT A and INPUT B as described in detail below. Pulse selector circuit 904 then provides signals to the D inputs of flip-flops 910 and 912.

On the next pulse in INPUT B, flip-flop 910 is set, thereby allowing $\overline{\text{PHASE B}}$ to transition to a high logic level. This also removes the clear signal from flip-flop 914. On the next negative edge of INPUT A, flip-flop 914 is set. This clears flip-flop 910 and the output $\overline{\text{PHASE B}}$ returns to a low logic level. Thus, flip-flops 910 and 914 combine to create a PHASE B signal with a duty cycle that is modulated with the phase difference between INPUT A and INPUT B.

B. Pulse Selector Circuit

Pulse selector circuit 904 is centered around the operation of four-bit counter 920. In this embodiment, counter 920 is programmable to operate with INPUT A and INPUT B comprising pulse streams of 5, 10 or 20 MHZ with 8, 16, and 32 pulses, respectively. At each frequency, pulse selector circuit 904 allows one-quarter of the pulses to pass and then selects the next one-quarter of the pulses.

Counter 920 is a counter that is loadable with an initial value. Initial values are loaded in counter 920 at two points in its operation. First, counter 920 is loaded with a value that selects the number of pulses to be allowed to pass before beginning the duty cycle modulation. Counter 920 counts from this initial value up to the value 8 (output Q3 is a high logic level). The difference between 8 and the initial value is the number of pulses that are allowed to pass before selecting pulses. For example, with a 5 MHZ signal, the initial value is set at 6 thus only two pulses are allowed to pass before pulses are selected.

Once counter 920 reaches the value 8, counter 920 is reloaded with a number that allows pulse selector circuit 904 to select the appropriate number of pulses. Again, the number of pulses that is allowed to pass is equal to the difference between 16 and the initial value. In the 5 MHZ example, counter 920 is loaded with the value 14, thus allowing 2 pulses to be selected.

The values loaded into counter 920 at each of these two points are selected based on the frequency of signals INPUT A and INPUT B. The values loaded into counter 920 are controlled by inputs D0–D3. The first set of values for 5, 10, and 20 MHZ is 6, 4, and 0 thus allowing 2, 4, and 8 pulses to pass, respectively. The second set of values for 5, 10, and 20 MHZ is 14, 12, and 8 thereby allowing 2, 4, and 8 pulses to be selected, respectively.

Pulse selector circuit 904 also includes a number of latches. First, latch 922 is enabled when the DETECT EN signal goes active. The output of latch 922 is provided through inverter 924 to OR gate 925, a clear input of latch 926, a clear input of latch 928, and the clear input of latch 938. Latch 926 latches when counter 920 reaches a count of 8. A D input of latch 926 is coupled to an output of OR gate 930. OR gate 930 is coupled to the Q3 output of counter 920 and the output of latch 926.

Latch 928 indicates when pulse selector circuit 904 has finished selecting pulses for duty cycle modulator 902. The D input of latch 928 is coupled to the output of AND gate 932. A first input of AND gate 932 is coupled to the output of latch 926 and a second input of AND gate 932 is coupled to the complement of the Q3 output of counter 920. The output of AND gate 932 is also coupled to the count enable (CE) input of counter 920 through inverter 934.

Pulse selector circuit 904 also includes logic circuitry that controls the loading of values into counter 920. OR gate 925 is coupled to the load (L) input of counter 920. As mentioned above, OR gate 925 receives one input from inverter 924. The other input of OR gate 925 is provided by AND gate 936. AND gate 936 has a first input coupled to the Q3 output of counter 920. Further, the other input of AND gate 936 is coupled to the complement of the output of latch 926. Counter 920 also includes inputs D0–D3 to receive values for loading into the counter. Input D0 is coupled to the Q3 output of counter 920. Input D1 is coupled to a 5 MHZ enable signal (EN5 MHz) that indicates whether INPUT A and INPUT B are 5 MHZ signals. Input D2 is coupled to a 20 MHZ enable signal (EN20 MHz) that is active when it is low. Finally, input D3 is coupled to the output Q3.

Pulse selector circuit 904 provides two inputs to duty cycle modulator 902. First, the Q3 output of counter 920 is provided directly to the D input of flip-flop 910. Second, the Q3 output of counter 920 is latched by latch 938 and provided to the D input of flip-flop 912.

The latches and counter 920 of pulse selector circuit 904 are clocked based on INPUT B.

In operation, pulse selector circuit 904 selects a number of pulses in the pulse trains of INPUT A and INPUT B. Initially, DETECT EN is at a low level. This holds latch 922 in a reset state. This allows the values of D0–D3 to be loaded into counter 920 through the control signal provided to the L input of counter 920 by inverter 924 and OR gate 925. When DETECT EN goes high, latch 922 is released from reset and the Q output of latch 922 goes high on the next rising edge of INPUT B. This reduces the output of inverter 924 to a low level. Thus, the load signal L returns to a low logic level and the counter 920 begins counting the pulses of INPUT B. Latch 926 is also released from reset. The output of latch 926 and the Q3 output operate through AND gate 932 and inverter 934 to provide a high logic level to the CE input of counter 920.

Counter 920 counts up from the initial value until it reaches 8. When counter 920 reaches 8, a high logic value at Q3 is provide to latch 926. This value is latched by latch 926 to indicate that the first half of the process is complete, namely, counting the pulses in INPUT B to allow to pass without creating a duty cycle modulated signal.

The high logic value at Q3 is also provided to latch 938 and to input D of flip-flop 910 to begin the duty cycle modulation process.

AND gate 936 and OR gate 925 load the next value into counter 920. Counter 920 then counts up until it rolls over to zero. This selects the number of pulses in the duty cycle modulated signals. At this point, Q3 is a low logic level. This changes the output of AND gate 932 to a high logic level which, when latched by latch 928, indicates the end of the process. Further, the CE input of counter 920 is reduced to a low logic level to end the counting process. The Q3 output sends low logic level signals to the D inputs of flip-flops 910 and 912 of duty cycle modulator 902.

X. Embodiment of a Transit Time Flow Meter

Figure 10:
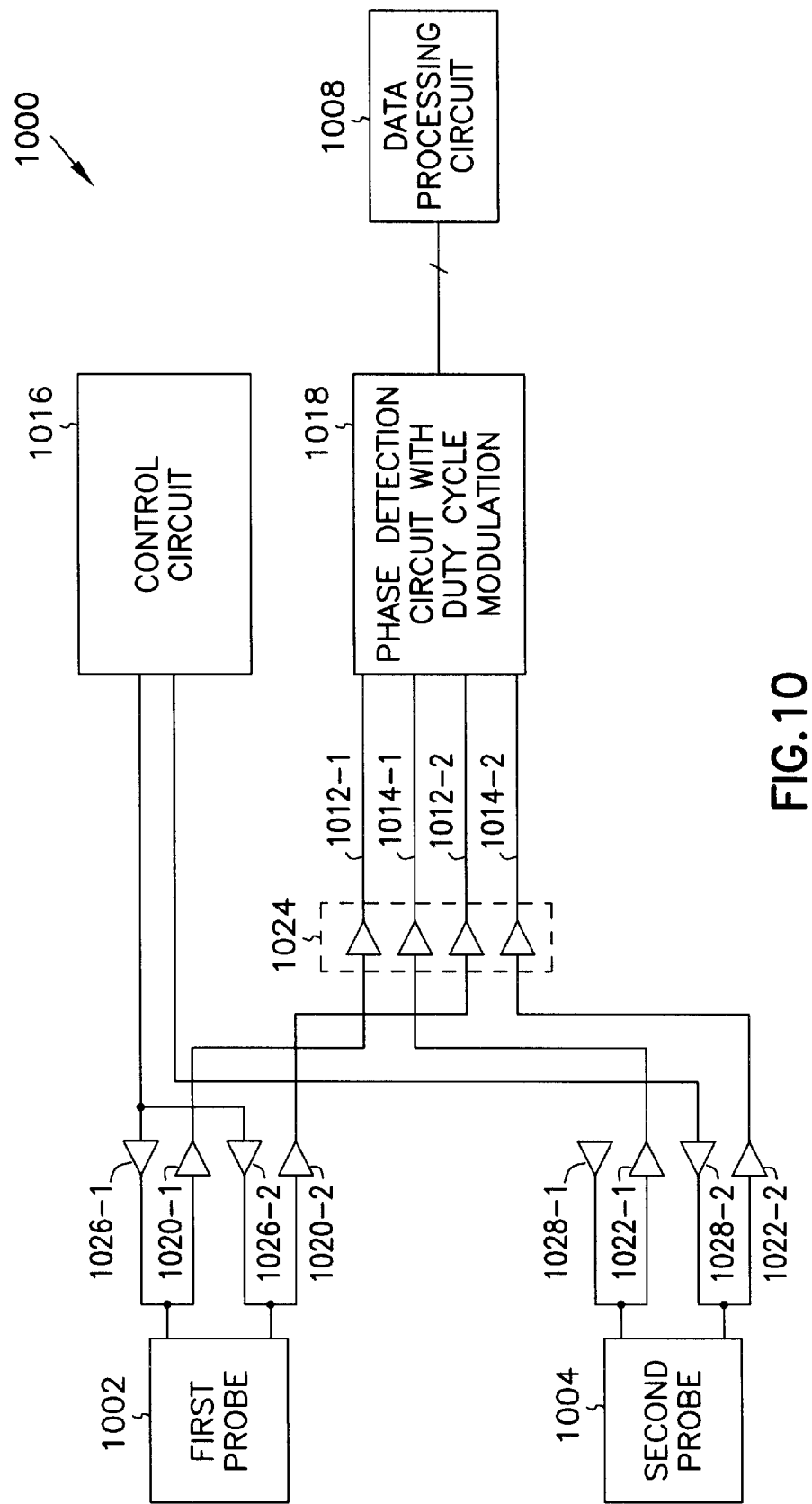
FIG. 10 is a block diagram of an embodiment of a transit time flow meter including a phase detector according to the teachings of the present invention.

FIG. 10 is a block diagram of a transit time flow meter indicated generally at 1000 and constructed according to the teachings of the present invention. Flow meter 1000 uses phase detection circuit 1018 to measure a time-shift in ultrasonic signals transmitted through fluid in a conduit by first and second probes 1002 and 1004, respectively. The time shift is processed by data processing circuit 1008 to produce, for example, flow data, or a volumetric flow measurement.

Phase detection circuit 1018 detects a phase difference or time-shift between first and second signals in two pair of input signals. Phase detection circuit 1018 is coupled to receive a first pair of input signals at inputs 1012-1 and 1014-1. Input 1012-1 is coupled to probe 1002 and input 1014-1 is coupled to second probe 1004. Phase detection circuit 1018 is also coupled to receive a pair of input signals at inputs 1012-2 and 1014-2. Input 1012-2 is coupled to first probe 1002 and input 1014-2 is coupled to second probe 1004. In one embodiment, phase detection circuit 1018 comprises two phase detection circuits constructed as shown and described above with respect to any one or more of FIGS. 1–9.

Phase detection circuit 1018 uses duty cycle modulation to generate at least two output signals. Each output signal is related to a time shift or phase difference between a selected pair of input signals.

First probe 1002 is coupled to inputs 1012-1 and 1012-2 of phase detection circuit 1018 to provide a first time-shift measurement through receivers 1020-1 and 1020-2. Second probe 1004 is coupled to inputs 1014-1 and 1014-2 of phase detection circuit 1018 to provide a second time-shift measurement through receivers 1022-1 and 1022-2.

In one embodiment, comparators 1024 are also provided at inputs 1012-1, 1012-2, 1014-1, and 1014-2. Comparators 1024 adjust the signals from first probe 1002 and second probe 1004 to be square waves.

Control circuit 1016 provides ultrasonic signals to first probe 1002 and second probe 1004 to create the time-shift signals provided to phase detection circuit 1018. Control circuit 1016 provides a first ultrasonic signal to first probe 1002 through pulsers 1026-1 and 1026-2. Pulsers 1026-1 and 1026-2 provide bursts of ultrasonic energy to a pair of transducers of first probe 1002. Similarly, control circuit 1016 provides a second control signal to pulsers 1028-1 and 1028-2 for a pair of transducers of second probe 1002.

Figure 11:
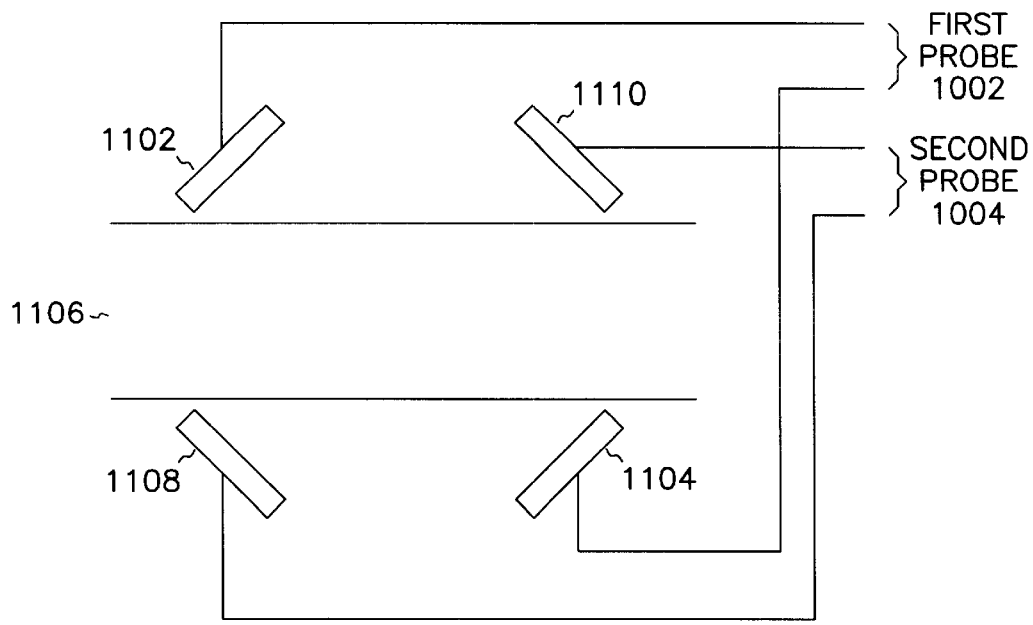
FIG. 11 is a block diagram of an embodiment of a probe for a transit time flow meter according to the teachings of the present invention.

One embodiment of first probe 1002 and second probe 1004 is shown by way of example in FIG. 11. As shown, first probe 1002 includes a pair of transducers 1102 and 1104 that are located on opposite sides of conduit 1106. Similarly, second probe 1004 includes a pair of transducers 1108 and 1110 that are also located on opposite sides of conduit 1106. Transducers 1102, 1104, 1108, and 1110 are disposed such that ultrasonic signals transmitted between the pairs of transducers form an X-pattern across a cross-section of conduit 1106. It is noted that in other embodiments, first and second probes 1002 and 1004 comprise independent probes.

Flow meter 1000 further includes data processing circuit 1008 that is coupled to the output of phase detection circuit 1018. In one embodiment, data processing circuit 1008 includes circuitry that transmits the output of phase detection circuit 1018 to a remote processor for processing to determine at least one flow rate. In other embodiments, data processing circuit 1008 is fabricated in a common housing with phase detection circuit 1018. In this embodiment, data processing circuit 1008 uses the output of phase detection circuit 1018 to calculate at least one flow rate. This data may be transmitted for use at a remote location.

In operation, flow meter 1000 measures the flow of fluid in a conduit, e.g., the volumetric flow of the fluid in conduit 1106 of FIG. 11. Initially, control circuit 1016 provides a first ultrasonic signal to first probe 1002 through pulsers 1026-1 and 1026-2. This ultrasonic signal contains a number of pulses that are transmitted from transducer 1102 to transducer 1104 and from transducer 1104 to transducer 1102. The received signals at transducers 1102 and 1104 are time-shifted due to the flow of fluid in conduit 1106. Phase detection circuit 1018 receives these signals at inputs 1012-1 and 1012-2. Phase detection circuit 1018 uses duty cycle modulation to detect a phase difference between the signals at inputs 1012-1 and 1012-2. This provides a first measurement to be used in calculating flow rate.

Control circuit 1016 then transmits the second ultrasonic signal to second probe 1004 through pulsers 1028-1 and 1028-2. This ultrasonic signal also contains a number of pulses that are transmitted from transducer 1108 to transducer 1110 and from transducer 1110 to transducer 1108. The received signals at transducers 1108 and 1110 are time-shifted due to the flow of fluid in conduit 1106. Phase detection circuit 1018 receives from receivers 1022-1 and 1022-2 these time-shifted signals. Phase detection circuit 1018 uses duty cycle modulation to detect a phase difference (time-shift) between these signals at inputs 1014-1 and 1014-2. This provides a second measurement to be used in calculating flow rate.

Data processing circuit 1008 uses the first and second measurements to calculate, e.g., a volumetric flow measurement. Alternatively, data processing circuit 1008 transmits the first and second measurements to a remote processor for calculating one or more flow measurements.

XI. Embodiment of a Phase Lock Loop

Figure 12:
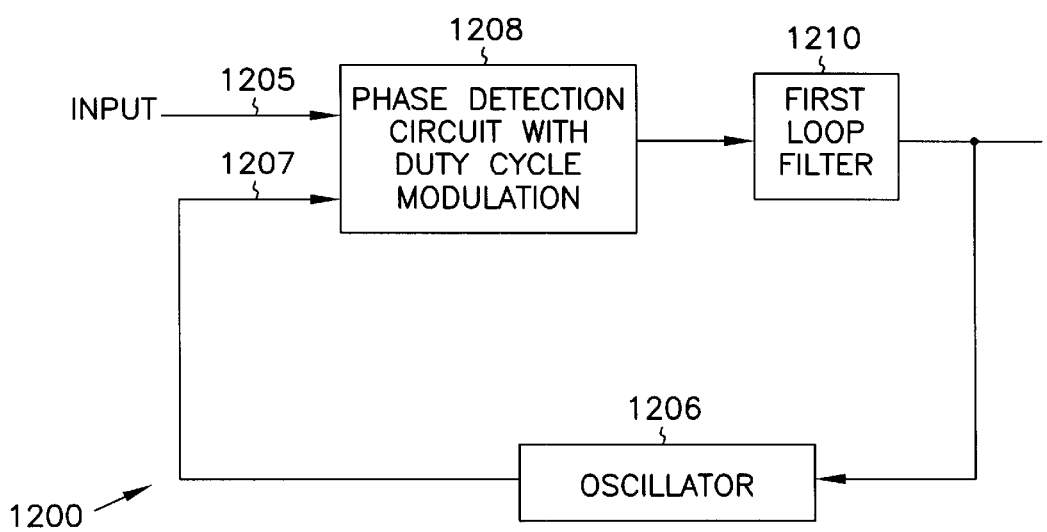
FIG. 12 is a block diagram of an embodiment of a phase lock loop according to the teachings of the present invention.

FIG. 12 is a block diagram of phase lock loop indicated generally at 1200 and constructed according to the teachings of the present invention. Phase lock loop 1200 includes phase detection circuit 1208. Phase detection circuit 1208 uses duty cycle modulation to detect a phase difference between an input signal at input 1205 and a feedback signal at input 1207. In one embodiment, phase detection circuit 1208 is constructed as shown and described above with respect to any one or more of FIGS. 1 through 9. Phase detection circuit 1208 provides output signals to loop filter 1210. Loop filter 1210 is coupled to an input of oscillator 1206. Oscillator 1206 provides an output to input 1207 of phase detection circuit 1208 as the feedback signal.

In operation, phase lock loop 1200 is operable to lock oscillator 1206 in phase and frequency with the input signal at input 1205. Phase detection circuit 1208 detects any phase difference between the signals at its inputs 1205 and 1207. This phase difference is provided to loop filter 1210 to adjust the settings for the oscillator 1206. In this manner, phase detection circuit 1208 controls the frequency and phase of oscillator 1206. Loop filter 1210 provides an output signal for phase lock loop 1200.

XII. Embodiment of Another Transit Time Flow Meter

Figure 13:
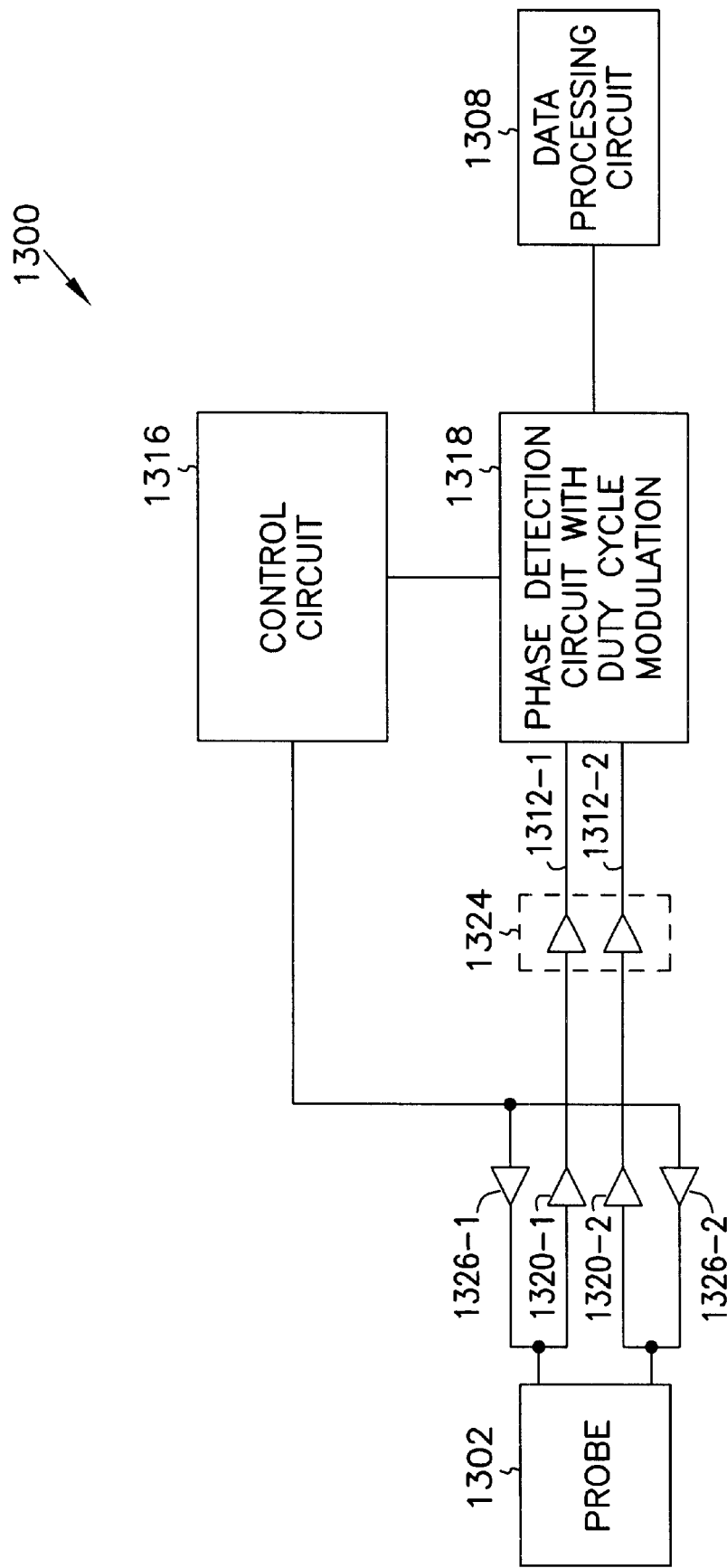
FIG. 13 is a block diagram of another embodiment of a transit time flow meter including a phase detector according to the teachings of the present invention.

FIG. 13 is a block diagram of a transit time flow meter indicated generally at 1300 and constructed according to the teachings of the present invention. Flow meter 1300 uses phase detection circuit 1318 to measure a time-shift in ultrasonic signals transmitted through fluid in a conduit by probe 1302. The time shift is processed by data processing circuit 1308 to produce, for example, flow data, or a volumetric flow measurement.

Phase detection circuit 1318 detects a phase difference or time-shift between first and second signals. Phase detection circuit 1318 is coupled to receive a pair of input signals at inputs 1312-1 and 1312-2. Inputs 1312-1 and 1312-2 are coupled to probe 1302. In one embodiment, phase detection circuit 1318 comprises a phase detection circuit constructed as shown and described above with respect to any one or more of FIGS. 1–9.

Phase detection circuit 1318 uses duty cycle modulation to generate at least one output signal. The output signal is related to a time shift or phase difference between the input signals.

Probe 1302 is coupled to inputs 1312-1 and 1312-2 of phase detection circuit 1318 to provide a time-shift measurement through receivers 1320-1 and 1320-2. In one embodiment, comparators 1324 are also provided at inputs 1312-1 and 1312-2. Comparators 1324 adjust the signals from probe 1302 to provide substantially square wave signals.

Control circuit 1316 provides ultrasonic signals to probe 1302 to create the time-shift signals provided to phase detection circuit 1318. Control circuit 1316 provides an ultrasonic signal to probe 1302 through pulsers 1326-1 and 1326-2. Pulsers 1326-1 and 1326-2 provide bursts of ultrasonic energy to a pair of transducers of probe 1302.

In one embodiment probe 1302 includes a pair of transducers that are located on opposite sides of a conduit.

Flow meter 1300 further includes data processing circuit 1308 that is coupled to the output of phase detection circuit 1318. In one embodiment, data processing circuit 1308 includes circuitry that transmits the output of phase detection circuit 1318 to a remote processor for processing to determine at least one flow rate. In other embodiments, data processing circuit 1308 is fabricated in a common housing with phase detection circuit 1318. In this embodiment, data processing circuit 1308 uses the output of phase detection circuit 1318 to calculate at least one flow rate. This data may be transmitted for use at a remote location.

In operation, flow meter 1300 measures the flow of fluid in a conduit, e.g., the volumetric flow of the fluid in a conduit. Initially, control circuit 1316 provides an ultrasonic signal to probe 1302 through pulsers 1326-1 and 1326-2. Phase detection circuit 1318 receives signals that are time-shifted due to the flow of fluid in the conduit at inputs 1312-1 and 1312-2. Phase detection circuit 1318 uses duty cycle modulation to detect a phase difference between the signals at inputs 1312-1 and 1312-2. This provides a measurement to be used in calculating flow rate.

Data processing circuit 1308 uses the measurement to calculate, e.g., a volumetric flow measurement. Alternatively, data processing circuit 1308 transmits the measurement to a remote processor for calculating one or more flow measurements.

Conclusion

Although specific embodiments have been illustrated and described herein, it will be appreciated by those of ordinary skill in the art that any arrangement which is calculated to achieve the same purpose may be substituted for the specific embodiment shown.

This application is intended to cover any adaptations or variations of the present invention. For example, the input signals can be duty cycle modulated using other conventional techniques. Further, current sources other than a current mirror may be used with the second stage of the phase detector, e.g., a bipolar junction transistor with a reference voltage coupled to its base. The differential output from the two sampling capacitors can also be provided as output with or without a reference voltage off-set. Further, the amplifier that provides the output of the second stage can be replaced with other circuitry that processes the analog signals produced by the second stage, e.g., one or more analog to digital converters.

What is claimed is:

1. A transit time flow meter, comprising:
    a first pair of transducers;
    a second pair of transducers;
    wherein the first and second pair of transducers are placeable in relation to a conduit to transmit ultrasonic signals through a fluid;
    a phase detector, coupled to the first and second pairs of transducers, the phase detector using duty cycle modulation to determine a first phase difference between signals received from the first pair of transducers and a second phase difference between signals received from the second pair of transducers, the phase detector being responsive to an enable signal for selectively sampling portions of the signals received from the first pair of transducers and the second pair of transducers at selectable sampling start times for a selectable number of pulses in the signals; and
    a data processing circuit, responsive to the phase detector, that generates a measure of fluid flow in the conduit based on the first and second phase differences.

2. The flow meter of claim 1, wherein the phase detector comprises first and second phase detectors each coupled to one of the first and second pair of transducers.

3. The flow meter of claim 2, wherein each phase detector comprises:
    a first stage that receives first and second input signals, modulates the duty cycle of first and second intermediate signals based on a phase difference between the first and second input signals and selects a number of pulses in the first and second intermediate signals; and
    a second stage that receives the selected pulses of the first and second intermediate signals and charges first and second capacitors using the first and second intermediate signals, respectively, to create a differential signal that is based on the phase difference between the first and second input signals.

4. The flow meter of claim 3, wherein the second stage includes:
    a first current source coupled to the first capacitor through a first switch, the first switch responsive to the first intermediate signal; and
    a second current source coupled to the second capacitor through a second switch, the second switch responsive to the second intermediate signal.

5. The flow meter of claim 4, wherein the first and second current sources comprise current mirrors.

6. The flow meter of claim 4, wherein:
    the first switch comprises a differential amplifier with a first input coupled to the first intermediate signal and a second input coupled to a complement of the first intermediate signal; and
    the second switch comprises a differential amplifier with a first input coupled to the second intermediate signal and a second input coupled to a complement of the second intermediate signal.

7. The flow meter of claim 3, wherein the second stage includes a circuit that clears the voltage on the first and second capacitors.

8. The flow meter of claim 3, wherein the second stage includes an instrumentation amplifier with first and second inputs coupled to the differential signal.

9. The flow meter of claim 8, wherein the instrumentation amplifier includes a reference voltage offset.

10. The flow meter of claim 3, wherein the first stage includes a logic circuit that increases the duration of the high logic level pulses of the first intermediate signal based on the phase difference between the first and second input signals and reduces the duration of the high logic level pulses of the second intermediate signal based on the phase difference between the first and second input signals.

11. The flow meter of claim 4, wherein the second stage includes a switch that decouples the first capacitor from the first switch and a switch that decouples the second capacitor from the second switch when reading the differential signal.

12. The flow meter of claim 1, wherein the data processing circuit includes a transmitter for transmitting data to a remote processor.

13. A method for detecting flow in a fluid, the method comprising:
   transmitting ultrasonic signals between first and second transducers;
   receiving time-shifted ultrasonic signals at the first and second transducers;
   sampling the time-shifted ultrasonic signals from the first and second transducers using a first enable signal, wherein the sampled time-shifted ultrasonic signals are capable of including selectable portions of the time-shifted ultrasonic signals from the first and second transducers beginning at selectable sampling start times for a selectable number of pulses in the ultrasonic signals;
   determining a first phase difference between the sampled time-shifted ultrasonic signals from the first and second transducers using duty cycle modulation;
   transmitting ultrasonic signals between third and fourth transducers;
   receiving time-shifted ultrasonic signals at the third and fourth transducers;
   sampling the time-shifted ultrasonic signals from the third and fourth transducers using a second enable signal, wherein the sampled time-shifted ultrasonic signals are capable of including selectable portions of the time-shifted ultrasonic signals from the third and fourth transducers beginning at selectable sampling start times for a selectable number of pulses in the ultrasonic signals;
   determining a second phase difference between the sampled time-shifted ultrasonic signals from the third and fourth transducers using duty cycle modulation; and
   generating a flow measurement based on the first and second phase differences.

14. The method of claim 13, wherein determining the first phase difference comprises:
   modulating a duty cycle of first and second intermediate signals from a first duty cycle based on a phase difference between the time-shifted ultrasonic signals from the first and second transducers; and
   creating a differential signal based on the modulated duty cycles of the first and second intermediate signals that is related to the phase difference between the time-shifted ultrasonic signals from the first and second transducers.

15. The method of claim 14, and further comprising selecting a number of pulses in the first and second intermediate signals.

16. The method of claim 14, wherein modulating the duty cycle comprises modulating the duty cycles of the first and second intermediate signals from nominal, fifty percent duty cycles.

17. The method of claim 14, wherein creating a differential signal comprises creating a differential output signal that is proportional to twice the phase difference between the time-shifted ultrasonic signals from the first and second transducers.

18. The method of claim 14, and further comprising converting the time-shifted ultrasonic signals from the first and second transducers to fifty percent duty cycles prior to modulating the duty cycles of the first and second intermediate signals.

19. The method of claim 14, wherein determining the second phase difference comprises:
   modulating a duty cycle of first and second intermediate signals from a first duty cycle based on a phase difference between the time-shifted ultrasonic signals from the third and fourth transducers; and
   creating at least one additional differential signal based on the modulated duty cycles of the first and second intermediate signals that is related to the phase difference between the time-shifted ultrasonic signals from the third and fourth transducers.

20. The method of claim 14, wherein generating a flow measurement based on the first and second phase differences comprises generating a volumetric flow measurement.

21. A transit time flow meter, comprising:
   a pair of transducers;
   wherein the pair of transducers are placeable in relation to a conduit to transmit ultrasonic signals through a fluid;
   a phase detector, coupled to the pair of transducers, the phase detector using duty cycle modulation to determine a phase difference between signals received from the pair of transducers, the phase detector being responsive to an enable signal for selectively sampling portions of the signals received from the pair of transducers at selectable start times for a selectable number of pulses of the signals; and
   a data processing circuit, responsive to the phase detector, that generates a measure of fluid flow in the conduit based on the phase difference.

22. The flow meter of claim 21, wherein the phase detector comprises:
   a first stage that receives first and second input signals, modulates the duty cycle of first and second intermediate signals based on a phase difference between the first and second input signals and selects a number of pulses in the first and second intermediate signals; and
   a second stage that receives the selected pulses of the first and second intermediate signals and charges first and second capacitors using the first and second intermediate signals, respectively, to create a differential signal that is based on the phase difference between the first and second input signals.

23. The flow meter of claim 22, wherein the second stage includes:
   a first current source coupled to the first capacitor through a first switch, the first switch responsive to the first intermediate signal; and
   a second current source coupled to the second capacitor through a second switch, the second switch responsive to the second intermediate signal.

24. The flow meter of claim 23, wherein the first and second current sources comprise current mirrors.

25. The flow meter of claim 23, wherein:
   the first switch comprises a differential amplifier with a first input coupled to the first intermediate signal and a second input coupled to a complement of the first intermediate signal; and
   the second switch comprises a differential amplifier with a first input coupled to the second intermediate signal and a second input coupled to a complement of the second intermediate signal.

26. The flow meter of claim 22, wherein the second stage includes a circuit that clears the voltage on the first and second capacitors.

27. The flow meter of claim 22, wherein the second stage includes an instrumentation amplifier with first and second inputs coupled to the differential signal.

28. The flow meter of claim 27, wherein the instrumentation amplifier includes a reference voltage offset.

29. The flow meter of claim 22, wherein the first stage includes a logic circuit that increases the duration of the high logic level pulses of the first intermediate signal based on the phase difference between the first and second input signals and reduces the duration of the high logic level pulses of the second intermediate signal based on the phase difference between the first and second input signals.

30. The flow meter of claim 23, wherein the second stage includes a switch that decouples the first capacitor from the first switch and a switch that decouples the second capacitor from the second switch when reading the differential signal.

31. The flow meter of claim 21, wherein the data processing circuit includes a transmitter for transmitting data to a remote processor.

32. A method for detecting flow in a fluid, the method comprising:

transmitting ultrasonic signals between first and second transducers;

receiving time-shifted ultrasonic signals at the first and second transducers;

sampling the time-shifted ultrasonic signals using an enable signal, wherein the sampled time-shifted ultrasonic signals are capable of including selectable portions of the time-shifted ultrasonic signals beginning at selectable sampling start times for a selectable number of pulses in the ultrasonic signals;

determining a phase difference between the time-shifted ultrasonic signals from the first and second transducers using duty cycle modulation; and generating a flow measurement based on the phase difference.

33. The method of claim 32, wherein determining the phase difference comprises:

modulating a duty cycle of first and second intermediate signals from a first duty cycle based on a phase difference between the time-shifted ultrasonic signals from the first and second transducers; and creating a differential signal based on the modulated duty cycles of the first and second intermediate signals that is related to the phase difference between the time-shifted ultrasonic signals from the first and second transducers.

34. The method of claim 33, and further comprising selecting a number of pulses in the first and second intermediate signals.

35. The method of claim 33, wherein modulating the duty cycle comprises modulating the duty cycles of the first and second intermediate signals from nominal, fifty percent duty cycles.

36. The method of claim 33, wherein creating a differential signal comprises creating a differential output signal that is proportional to twice the phase difference between the time-shifted ultrasonic signals from the first and second transducers.

37. The method of claim 33, and further comprising converting the time-shifted ultrasonic signals from the first and second transducers to fifty percent duty cycles prior to modulating the duty cycles of the first and second intermediate signals.

38. The method of claim 33, wherein generating a flow measurement based on the phase difference comprises generating a volumetric flow measurement.

* * * * *